(12) United States Patent
Dalko et al.

(10) Patent No.: US 11,045,411 B2
(45) Date of Patent: Jun. 29, 2021

(54) PROCESS FOR TREATING KERATIN MATERIALS USING AMIDE, ACID OR ESTER C-GLYCOSIDE DERIVATIVES, AND COSMETIC COMPOSITION CONTAINING SAME

(71) Applicant: L'OREAL, Paris (FR)

(72) Inventors: Maria Dalko, Versailles (FR); Marie-céline Frantz, Aulnay-sous-Bois (FR); Amélie Gueguiniat, Autheuil en Valois (FR); Jinzhu Xu, Paris (FR); Lisheng Mao, Shangai (CN)

(73) Assignee: L'OREAL, Paris (FR)

(*) Notice: Subject to any disclaimer, the term of this patent is extended or adjusted under 35 U.S.C. 154(b) by 552 days.

(21) Appl. No.: 15/571,951

(22) PCT Filed: May 9, 2016

(86) PCT No.: PCT/EP2016/060299
§ 371 (c)(1),
(2) Date: Nov. 6, 2017

(87) PCT Pub. No.: WO2016/177908
PCT Pub. Date: Nov. 10, 2016

(65) Prior Publication Data
US 2018/0133137 A1 May 17, 2018

(30) Foreign Application Priority Data
May 7, 2015 (FR) ...................................... 1554157

(51) Int. Cl.
*A61K 8/365* (2006.01)
*A61K 8/60* (2006.01)
*A61Q 19/08* (2006.01)
*C07H 7/02* (2006.01)

(52) U.S. Cl.
CPC .............. *A61K 8/602* (2013.01); *A61K 8/365* (2013.01); *A61Q 19/08* (2013.01); *C07H 7/02* (2013.01)

(58) Field of Classification Search
None
See application file for complete search history.

(56) References Cited

U.S. PATENT DOCUMENTS

| | | | |
|---|---|---|---|
| 5,900,232 A | 5/1999 | Cauwet et al. | |
| 2005/0002889 A1 | 1/2005 | Dalko et al. | |
| 2005/0113313 A1 | 5/2005 | Beljanin et al. | |

FOREIGN PATENT DOCUMENTS

| | | |
|---|---|---|
| FR | 2 901 133 A1 | 11/2007 |
| JP | 2010 195687 A | 9/2011 |
| WO | WO 94/27575 A1 | 12/1994 |
| WO | WO 99/15510 A1 | 4/1999 |
| WO | WO 2010/004269 A2 | 1/2010 |
| WO | WO 2012/023584 A1 | 2/2012 |

OTHER PUBLICATIONS

Schweizer et al (Organic Lett 3:4115-4118, 2001) (Year: 2001).*
Lopez-Herrera et al (J Org Chem 62:6056-6059, 1997) (Year: 1997).*
Schweizer et al. "Chain Extension of Sugar [delta]-Lactones with the Enolate of tert-Butyl Bromoacetate and Elaboration into Functionalized C-Ketosides, C-Glycosides, and C-Glycines", Organic Letters, vol. 3, No. 25, 2001, pp. 4115-4118, XP055210025.
Brar A et al, "Synthesis of chiral non-proteinogenic 4,5-di hydroxytetrahydropyran derived alpha-amino acids from D-mannitol", Tetrahedron Letters, vol. 47, No. 51, 2006, pp. 9035-9038, XP025005177.
Database PubChem [Online]; Database accession No. CID 91359529, Mar. 17, 2015, XP55278787.
Yang et al., "Studies on the synthesis of Di-and trisaccharide analogues of moenomycin A. Modifications in unit E and in the lipid part", Helvetica Chimica Acta, vol. 87, 2004, XP002404113.
Palasz et al., "Application of 2,4,6-trioxo-pyrimidin-5-ylidene alditols in the synthesis of pyrano[2,3-d]pyrimidines containing a sugar moiety by hetero-Diels-Alder reactions and by conjugate Michael addition-cyclizations", Tetrahedron, vol. 69, No. 38, Jul. 16, 2013, pp. 8216-8227, XP028688565.
Scherrmann et al., "Functionalization of Carbohydrates in Water", Handbook of Green Chemistry, vol. 5: Reactions in Water, 2010, XP055311633.
Gannett et al., "In Vitro Reaction of Barbiturates with Formaldehyde", Journal of Analytical Toxicology., vol. 25, No. 6, 2001, pp. 443-449, XP055311675.
Carpenter et al., "Modifications in the nitric acid oxidation of D-mannose: X-ray crystal structure of N,N'-dimethyl D-mannaramide", Carbohydrate Research, vol. 376, 2013, pp. 29-36, XP028571342.

* cited by examiner

*Primary Examiner* — Craig D Ricci
(74) *Attorney, Agent, or Firm* — Polsinelli PC

(57) ABSTRACT

The present invention relates to a process for cosmetic treatment of the skin, comprising the application to the skin of a composition comprising a compound (I)

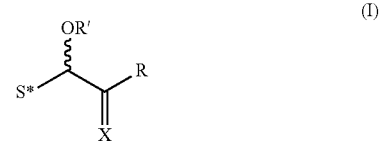

with R, R' and X as defined in the description and S* a monosaccharide or polysaccharide.

7 Claims, No Drawings

PROCESS FOR TREATING KERATIN MATERIALS USING AMIDE, ACID OR ESTER C-GLYCOSIDE DERIVATIVES, AND COSMETIC COMPOSITION CONTAINING SAME

CROSS REFERENCE TO RELATED APPLICATIONS

This application is a National Phase filing under 35 U.S.C. § 371 of PCT/EP2016/060299 filed on May 9, 2016; and this application claims priority to Application No. 1554157 filed in France on May 7, 2015 under 35 U.S.C. § 119. The entire contents of each application are hereby incorporated by reference.

The invention relates to novel C-glycoside compounds comprising an amide, acid or ester group, to a cosmetic composition comprising same, to a preparation process, to the use of said C-glycosides for treating keratin materials and in particular the skin, and to a process for treating keratin materials using said C-glycosides.

In particular, said C-glycosides of the invention are inducers of GLUT-1 expression.

The present invention relates in particular to the field of aging and of the signs that are associated therewith, on the skin and/or skin appendages. It relates in particular to the modulation of the equilibrium between epidermal cell proliferation and differentiation and to the improvement of the signs associated with the phenomenon of epidermal thinning due to a decrease in the number of keratinocytes in the proliferation phase.

Women, and men, currently have a tendency to wish to appear youthful for as long as possible and consequently seek to tone down the signs of aging on the skin, which are reflected in particular by wrinkles and fine lines, thinning of the epidermis and/or a flaccid and withered skin appearance. In this regard, the advertising and fashion industries mention products for retaining radiant and wrinkle-free skin, signs of youthful skin, for as long as possible, all the more so since physical appearance has an effect on the psyche and/or on morale.

The skin is constituted of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these types of cells contributes, by virtue of its intrinsic functions, to the essential role played in the body by the skin, in particular the role of protecting the body against external attacking factors, which is known as the "barrier function".

The epidermis is conventionally divided into a basal layer of keratinocytes that constitutes the germinative layer of the epidermis, a spinous layer constituted of several layers of polyhedral cells positioned on the germinative layers, one to three "granular" layers constituted of flattened cells containing distinct cytoplasmic inclusions, keratohyalin granules, and finally the cornified layer (or stratum corneum), constituted of a set of layers of keratinocytes at the terminal stage of their differentiation, known as corneocytes. Corneocytes are anuclear cells mainly constituted of a fibrous material containing cytokeratins, surrounded by a cornified envelope.

The dermis provides the epidermis with a solid support. It is also its nourishing element. It is constituted mainly of fibroblasts and an extracellular matrix composed predominantly of collagen, elastin and a substance known as ground substance. These components are synthesized by the fibroblasts. Leukocytes, mast cells or else tissue macrophages are also found therein. Finally, blood vessels and nerve fibers pass through the dermis. The cohesion between the epidermis and the dermis is provided by the dermo-epidermal junction.

The epidermis is constantly engaged in producing new keratinocytes to compensate for the continuous loss of epidermal cells at the cornified layer. However, in the course of aging, a decrease in the number of cells in the proliferation phase, and consequently a decrease of the live epidermal layers, may be observed physiologically. By limiting and/or delaying the passing of cells into the differentiation phase, the pool of young cells is maintained.

It is thus important to preserve this pool of proliferative cells, by preventing or delaying their differentiation, in order to contribute towards delaying the onset of the signs of aging.

Glucose transport in most mammalian cells is regulated by a family of membrane proteins called "glucose transporters", also denoted GLUT. At least 13 proteins are encoded by a family of related genes, these proteins having various transmembrane domains. Expression of the various GLUT isoforms varies depending on the tissue and the hormonal and environmental conditions.

Keratinocytes express at least 4 types of glucose transporters, GLUT-1, 2, 3 and 5. In the prior art, a certain number of applications are described with GLUT inducers.

Thus, US 2003/0187036 proposes the use of biguanide derivatives for promoting the healing of skin lesions such as ulcers occurring in diabetics, or other injuries.

Thus, US 2005/0037440 relates to the identification of longevity factors in mammals, and to the role of the cJUN factor in the modulation of the JNK signal. It thus suggests using agents that decrease the activity of an indicator such as DAF-14, superoxide dismutase, GLUT-1 or GLUT-4, for combating the signs of age is caused mainly by oxidative stress.

DE 10259966 describes cosmetic or pharmaceutical compositions which contain amino acids of mycosporine type and which improve oxygen uptake; these compounds induce in particular a reduction in GLUT-1 expression. The compositions can in particular be applied to the treatment of skin aging.

FR2901133 describes the use, in a composition containing a physiologically acceptable medium, of at least one compound that induces epidermal glycolysis (with the exclusion of IGF-1), as an agent for decreasing and/or delaying the signs of aging of the skin and/or of skin appendages. Advantageously, the glycolysis-inducing compound is a glucose transporter (GLUT) peptide activator.

However, there is still a need to find novel useful anti-aging agents.

Moreover, glycosides are very advantageous in varied fields, including the cosmetics industry; nevertheless, their chemical synthesis, in particular for C-glycosides, is not always easy and accessible. Indeed, it is generally necessary either to halogenate the carbon atom in position 1 of the sugar, then to subject it to substitution reactions by alkylation, organomagnesium compounds, organolithium compounds, etc., having previously taken care to protect the hydroxyl or amino groups of the sugar, and then to subsequently deprotect them (see, for example, "*recent advances in stereoselective C-glycoside synthesis*", tetrahedron, 54, 9913-9959 (1998)), or another solution is to use glycosylation by catalysis with transition metals. However, the use thereof is not always easy and in addition requires the use of metal catalysts and ligands that are expensive, and not necessarily industrial, and that must be compatible with the cosmetic use of the C-glycosides synthesized (see, for example, "recent advances in transition metal catalyzed glycosylation" ACS catal 3, 2(8), 1563-1595 (2012)). In addition, these synthesis routes do not make it possible to obtain, from one and the same reagent, amides, esters or acids of sugars without having to use the protection and deprotection of the hydroxyl or amino groups. Furthermore, most of the reactions for obtaining C-glycosides are carried out in solvents that are not always eco-compatible or are difficult to use industrially. It is therefore desirable, as much as possible, to use solvents that are cosmetically acceptable and eco-compatible, and in particular water.

Moreover, during chronological and/or actinic aging, the dermis and the epidermis undergo numerous modifications and degradations which are reflected, with age, by flaccidness and a loss of suppleness of the skin.

Among the components degraded (in particular collagen and elastin), proteoglycans (also referred to as PGs) and glycosaminoglycans (also referred to as GAGs) are also adversely affected. Specifically, over the course of aging, the fibroblasts and keratinocytes produce fewer and fewer PGs and GAGs and the synthesis thereof is imperfect. This results in significant disorganization: the deposition of GAGs on the protein backbone forming the PG is abnormal, which results in a decrease in the tonicity of the tissues and therefore in suppleness of the skin.

The compounds (I), and in particular the compounds (Ic) described below, used according to the invention also have good skin desquamation activity.

The applicant has surprisingly demonstrated that certain C-glycoside compounds comprising an amide, ester or acid group have anti-aging properties.

In addition, the applicant has found an easy means of synthesis for obtaining a large variety of C-glycosides, in particular by using a barbituric acid derivative and then an oxidizing agent such as hydrogen peroxide or a hydrogen peroxide-generating system. This method is compatible with sugar units comprising hydroxyl and optionally amino functions that are not protected.

A subject of the present invention is therefore the cosmetic use of a C-glycoside compound of formula (I) as defined below as an anti-aging agent.

Another subject of the invention is novel compounds of formula (I) as defined below.

The compounds (I) and (I''') make it possible in particular to treat keratin materials and in particular the skin, in particular for decreasing and/or delaying the signs of aging of the skin and/or of skin appendages.

The invention also relates to a process for cosmetic treatment of keratin materials, in particular of the skin, comprising the application to said materials of a cosmetic composition comprising at least one compound of formula (I) or (I''').

The term "skin" is intended to mean facial and/or bodily skin and the scalp.

The term "skin appendages" is intended to mean the eyelashes, the eyebrows, the nails and the hair, in particular the eyelashes and the hair.

According to another particular embodiment of the invention, the composition is intended for topical administration to keratin materials such as the skin.

The compounds (I) and (I''') make it possible in particular to prevent and/or treat the signs of skin aging.

Among the signs of skin aging, mention is in particular made of a loss of firmness and/or elasticity and/or tonicity and/or suppleness of the skin, the formation of wrinkles and fine lines, expression lines, in particular on the forehead and in the space between the eyebrows, perioral wrinkles and/or fine lines, and/or slackening in the area around the lips, in particular in the top lip area (area between the top lip and the nose), a dull appearance of the complexion, and the papery appearance of the skin.

The compounds (I) and (I''') advantageously have a glycosaminoglycan-synthesis-stimulating activity and thus make it possible to prevent and/or treat the signs of skin aging, in particular the loss of firmness and/or of elasticity and/or tonicity and/or of suppleness of the skin.

A first subject of the invention is a process for treating keratin materials, using at least one cosmetic composition comprising at least one compound of formula (I) below:

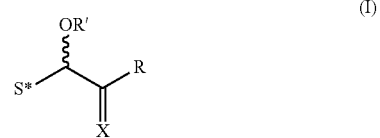

and also the solvates thereof such as hydrates, the optical and geometric isomers and tautomers thereof and the organic or mineral base or acid salts thereof, in which formula (I):

S* denotes a monosaccharide sugar radical or denotes a polysaccharide sugar radical comprising from 2 to 5 saccharide units, preferably from 2 to 3 saccharide units, preferentially S* denotes a sugar radical comprising 1 or 2 saccharide unit(s) (monosaccharide or disaccharide), each saccharide unit (the saccharide unit in the case of a monosaccharide or each saccharide unit in the case of polysaccharides) comprising one or more hydroxyl groups optionally substituted with a radical R" chosen from:
i) $(C_1-C_6)$alkyl, $(C_2-C_6)$alkenyl, or $(C_2-C_6)$alkynyl; or
ii) an acetyl radical; or
iii) a protective group (PG) for hydroxyl function(s), such as $(C_2-C_6)$alkyl(thio)carbonyl, preferably $(C_2-C_6)$alkylcarbonyl;
in particular, R" represents a $(C_1-C_6)$alkyl group such as methyl, or an acetyl group; said monosaccharide or polysaccharide radical also possibly comprising one or more amino groups $NR_bR_c$ with $R_b$ and $R_c$, which may be identical or different, representing a hydrogen atom or an acetyl group, or a protective group for the amino function, such as $(C_2-C_6)$alkyl (thio)carbonyl, in particular $(C_2-C_6)$alkylcarbonyl; more particularly, $NR_bR_c$ represents a group $NHR_b$ with $R_b$ as defined above, and in particular $R_b$ denoting a hydrogen atom or an acetyl radical;
said monosaccharide or polysaccharide radical being connected to the rest of the molecule by a bond between the $C_1$ carbon atom of one of the sugars of said monosaccharide or polysaccharide radical, this bond possibly being α or β anomeric;

X represents an oxygen or sulfur atom or $N(R_d)$, with $R_d$ representing a hydrogen atom or a $(C_1-C_6)$alkyl group, or an aryl group such as phenyl; preferably, X represents an oxygen atom;

R' represents i) a hydrogen atom; ii) a $(C_1-C_{18})$alkyl group; iii) a $(C_2-C_{18})$alkenyl group; iv) a $(C_2-C_{18})$ alkynyl group, preferably a $(C_1-C_6)$alkyl group such as methyl, or v) a protective group (PG) for the hydroxyl function, such as $(C_1-C_{18})$alkyl(thio)carbonyl, $(C_2$-

$C_{18}$)alkenyl(thio)carbonyl or an aryl($C_1$-$C_4$)alkyl radical, optionally substituted in particular with at least one hydroxyl and/or saturated or unsaturated ($C_1$-$C_4$) alkoxy group; in particular an aryl($C_1$-$C_4$)alkyl radical such as benzyl, or a ($C_1$-$C_{18}$)alkylcarbonyl radical, preferably acetyl, or a ($C_2$-$C_{18}$)alkenylcarbonyl radical;

R represents a group chosen from: i) hydroxyl; ii) saturated or unsaturated ($C_1$-$C_{18}$)alkoxy, preferably ($C_1$-$C_6$)alkoxy, such as methoxy, ethoxy, isopropyloxy, tert-butyloxy or prenyloxy; iii) optionally substituted aryloxy such as phenyloxy or phenoxy; iv) optionally substituted aryl($C_1$-$C_6$)alkoxy such as benzyloxy; and iv) amino —$NR_1R_2$ with $R_1$ and $R_2$, which may be identical or different, representing a hydrogen atom, an aryl($C_1$-$C_4$)alkyl group which is optionally substituted in particular with at least one hydroxyl and/or saturated or unsaturated ($C_1$-$C_4$)alkoxy group; such as benzyl, ($C_1$-$C_{18}$)alkyl, ($C_2$-$C_{18}$)alkenyl, ($C_2$-$C_{18}$)alkynyl; preferably $C_1$-$C_{16}$ alkyl group such as methyl, n-propyl, n-hexyl, n-tetradecyl (n-$C_{14}$), or else $R_1$ and $R_2$ form, with the nitrogen atom to which they are attached, an optionally substituted heterocycloalkyl, such as piperazino, piperidino or morpholino.

Preferably, the hydroxyl radicals of the radical S* are not substituted or are all substituted with the same group R" as defined above, in particular with an acetyl group.

Preferably, the optional amino group(s) $NR_bR_c$ of the radical S* denote(s) $NHR_b$ with $R_b$ all denoting a hydrogen atom or all denoting an acetyl group.

Another subject of the invention is the use of the compounds of formula (I) as defined above, and preferentially the use of the compounds of formula (I'''), for cosmetic treatment of keratin materials

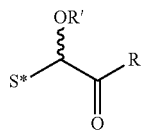

(I''')

and also the solvates thereof such as hydrates, the optical and geometric isomers and tautomers thereof and the organic or mineral base or acid salts thereof, in which formula (I'''), S* and R are as defined above, it being understood that they do not comprise a protective group (PG), and R' denotes a hydrogen atom, acetyl, ($C_1$-$C_{18}$)alkyl, ($C_2$-$C_{18}$)alkenyl or an aryl($C_1$-$C_4$)alkyl radical which is optionally substituted in particular with at least one hydroxyl and/or saturated or unsaturated ($C_1$-$C_4$)alkoxy group, in particular an aryl($C_1$-$C_4$)alkyl radical such as benzyl.

For the purposes of the present invention and unless otherwise indicated:

the saturated or unsaturated and optionally fused rings may also be optionally substituted;

the "alkyl" radicals are saturated, linear or branched, generally $C_1$-$C_{18}$, particularly $C_1$-$C_{10}$, hydrocarbon-based radicals, preferably $C_1$-$C_6$ alkyl radicals, such as $C_1$-$C_{14}$ alkyl group; mention may in particular be made of methyl, ethyl, isopropyl, n-propyl, n-butyl, t-butyl, isobutyl, sec-butyl, pentyl, isopentyl, neopentyl, n-hexyl, n-heptyl and octyl groups;

the "alkenyl" radicals are linear or branched, unsaturated $C_2$-$C_{18}$ hydrocarbon-based radicals; preferably comprising one or more conjugated or unconjugated double bonds, such as ethylene, propylene, butylene, pentylene, 2-methylpropylene, prenyl and decylene;

the "alkynyl" radicals are linear or branched, unsaturated $C_2$-$C_{18}$ hydrocarbon-based radicals, preferably comprising one or more triple bonds;

the "aryl" radicals are monocyclic or fused or non-fused polycyclic carbon-based radicals preferentially comprising from 6 to 30 carbon atoms, at least one ring of which is aromatic; preferentially, the aryl radical is chosen from phenyl, biphenyl, naphthyl, indenyl, anthracenyl and tetrahydronaphthyl;

the "alkoxy" radicals are alkyloxy radicals with alkyl as defined above, the alkyl part of the alkoxy generally being $C_1$-$C_{18}$, preferably $C_1$-$C_{10}$, such as methoxy, ethoxy, propoxy and butoxy; when mention is made of unsaturated, this implies that the alkoxy group can represent an alkenyloxy or alkynyloxy group with alkenyl and alkynyl as defined above;

the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;

the "heterocycloalkyl" radicals are saturated or partially unsaturated, nonaromatic heterocyclic radicals comprising from 4 to 8 ring members, which comprise from 1 to 3 heteroatoms, in particular chosen from oxygen, sulfur and nitrogen, preferably the morpholino, piperazino and piperidino radicals; the heterocycloalkyl radicals may be radicals which are substituted, in particular with alkyl, alkoxy, carboxylic acid, hydroxyl, amine and ketone groups;

the "aryl" or "heteroaryl" radicals can be substituted with at least one atom or group borne by at least one carbon atom, chosen from:

i) ($C_1$-$C_{10}$)alkyl, preferably $C_1$-$C_8$ alkyl, optionally unsaturated with one or more radicals chosen from the following radicals: hydroxyl, optionally substituted ($C_1$-$C_4$)alkoxy, (poly)hydroxy($C_2$-$C_4$)alkoxy, acylamino, amino substituted with two identical or different $C_1$-$C_4$ alkyl radicals optionally bearing at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another nitrogen or non-nitrogen heteroatom; ii) halogen; iii) hydroxyl; iv) $C_1$-$C_2$ alkoxy; v) $C_1$-$C_{10}$ alkoxycarbonyl; vi) (poly)hydroxy($C_2$-$C_4$)alkoxy; vii) amino; viii) 5- or 6-membered heterocycloalkyl; ix) 5- or 6-membered heteroaryl, optionally substituted with a ($C_1$-$C_4$)alkyl radical preferentially methyl; x) amino substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —$N^+R'R''R'''$, a for which R', R" and which may be identical or different, represent a hydrogen atom or a $C_1$-$C_4$ alkyl group; and a represents the anionic counterion such as the halide, d) one 5- or 6-membered heteroaryl radical, optionally substituted with a ($C_1$-$C_4$)alkyl radical, preferentially methyl; xi)

acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; xii) carbamoyl (($R)_2$N—C(O)—) in which the R radicals, which may be identical or different, represent a hydrogen atom or a $C_1$-$C_4$ alkyl radical optionally bearing at least one hydroxyl group; xiii) alkylsulfonylamino (R'S$(O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; xiv) aminosulfonyl (($R)_2$N—S$(O)_2$—) in which the radicals R, which may be identical or different, represent a hydrogen atom or a $C_1$-$C_4$ alkyl radical optionally bearing at least one hydroxyl group; xv) carboxyl in the acid or salified form (preferably salified with an alkali metal or a substituted or unsubstituted ammonium); xvi) cyano; xvii) nitro; xviii) polyhaloalkyl, preferentially trifluoromethyl; xix) a phenylcarbonyloxy group optionally substituted with one or more hydroxyl groups; xx) a phenyl group optionally substituted with one or more hydroxyl groups;

the "heteroaryl" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups, and at least one ring of which is aromatic. These rings may comprise one or more oxo groups on the carbon atoms of heteroaryl; mention may in particular be made, among the heterocyclic radicals that may be used, of furyl, pyranyl, pyrrolyl, imidazolyl, pyrazolyl, pyridyl thienyl, and pyrimidinyl groups; even more preferentially, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups;

the "protective group" or "PG" for the "hydroxyl" or "amino" function is known by those skilled in the art; mention may be made of the two books "Protective Groups in Organic Synthesis", T. W. Greene, published by John Wiley & Sons, NY, 1981, pp. 193-217; "Protecting Groups", P. Kocienski, Thieme, 3rd ed., 2005.

In particular, the protective group is chosen from:
- ($C_1$-$C_6$)alkyl(thio)carbonyl such as formyl, acetyl or t-butylcarbonyl;
- (di)(tri)halo($C_1$-$C_6$)alkyl(thio)carbonyl such as trifluoroacetyl (TFA);
- ($C_1$-$C_6$)alkoxy(thio)carbonyl such as methoxycarbonyl, ethoxycarbonyl, isobutyloxycarbonyl, t-butyloxycarbonyl (BOC), vinyloxycarbonyl, allyloxycarbonyl;
- (di)(tri)halo($C_1$-$C_6$)alkoxy(thio)carbonyl such as 2,2,2-trichloroethylcarbonyl;
- ($C_1$-$C_6$)alkylthiothiocarbonyl;
- (di)(tri)halo($C_1$-$C_6$)alkylthiothiocarbonyl;
- (di) ($C_1$-$C_6$) (alkyl)aminocarbonyl;
- (di) ($C_1$-$C_6$) (alkyl)aminothiocarbonyl;
- optionally substituted arylcarbonyl such as phenylcarbonyl or 2,4,6-trimethylphenylcarbonyl;
- optionally substituted aryloxycarbonyl such as p-nitrophenoxycarbonyl;
- optionally substituted aryl($C_1$-$C_6$)alkoxycarbonyl such as benzyloxycarbonyl or Cbz, p-methoxybenzyloxycarbonyl, 3,4-dimethoxybenzyloxycarbonyl, o-nitrobenzyloxycarbonyl, p-nitrobenzyloxycarbonyl, 2-bromobenzyloxycarbonyl (2-bromo-Z) and 2-chlorobenzyloxycarbonyl (2-chloro-Z), 4-nitrobenzyloxycarbonyl (nitro-Z);
- heteroaryl($C_1$-$C_6$)alkoxycarbonyl such as 9-fluorenylmethoxycarbonyl (FMOC) or nicotinoyl;
- (di) ($C_1$-$C_6$) (alkyl)aminocarbonyl such as dimethylaminocarbonyl;
- ($C_1$-$C_6$)(alkyl)arylaminocarbonyl;
- carboxyl;
- optionally substituted aryl such as phenyl, dibenzosuberyl or 1,3,5-cycloheptatrienyl;
- optionally substituted heteroaryl; in particular including the cationic or noncationic heteroaryls comprising from 1 to 4 heteroatoms below:

i) 5-, 6- or 7-membered monocyclic groups such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) 8- to 11-membered bicyclic groups such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$)alkyl, for instance methyl, or polyhalo($C_1$-$C_4$)alkyl, for instance trifluoromethyl;

iii) or the following tricyclic ABC group:

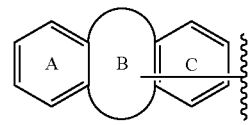

in which the two rings A and C optionally comprise a heteroatom, and ring B is a 5-, 6- or 7-membered ring, particularly a 6-membered ring, and contains at least one heteroatom, for instance piperidyl or pyranyl;

optionally cationic, optionally substituted heterocycloalkyl, the heterocycloalkyl group in particular representing a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl, di/tetrahydropyrimidinyl, these groups being optionally substituted with one or more groups such as ($C_1$-$C_4$) alkyl, oxo or thioxo, preferably tetrahydropyranyl THP; or the heterocycle represents the following group:

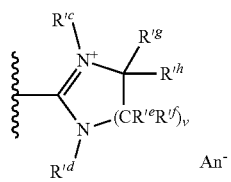

in which $R^{\prime c}$, $R^{\prime d}$, $R^{\prime e}$, $R^{\prime f}$, $R^{\prime g}$ and $R^{\prime h}$, which may be identical or different, represent a hydrogen atom or a ($C_1$-$C_4$)alkyl group, or alternatively two groups $R^{\prime g}$ with $R^{\prime h}$, and/or $R^{\prime e}$ with $R^{\prime f}$ form an oxo or thioxo group, or alternatively $R^{\prime g}$ with $R^{\prime e}$ together form a cycloalkyl; and v represents an integer between 1 and 3 inclusive; preferentially, $R^{\prime c}$ to $R^{\prime h}$ represent a hydrogen atom; and An⁻ represents a counterion;

isothiouronium —C(NR$^{\prime c}$R$^{\prime d}$)=N⁺R$^{\prime e}$R$^{\prime f}$; An⁻ with R$^{\prime c}$, R$^{\prime d}$, R$^{\prime e}$ and R$^{\prime f}$, which may be identical or different, representing a hydrogen atom or a ($C_1$-$C_4$)alkyl group; preferentially, $R^{\prime c}$ to $R^{\prime f}$ represent a hydrogen atom; and An⁻ represents a counterion;

isothiourea —C(NR$^{\prime c}$R$^{\prime d}$)=NR$^{\prime e}$; with R$^{\prime c}$, R$^{\prime d}$ and R$^{\prime e}$ as defined above;

optionally substituted (di)aryl($C_1$-$C_4$)alkyl or triaryl ($C_1$-$C_4$)alkyl such as 9-anthracenylmethyl, phenylmethyl (benzyl), diphenylmethyl or triphenylmethyl optionally substituted with one or more groups, in particular chosen from halogen, ($C_1$-$C_4$)alkyl, ($C_1$-$C_4$)alkoxy such as methoxy, hydroxyl, ($C_1$-$C_4$)alkylcarbonyl, (di)($C_1$-$C_4$)(alkyl)amino such as dimethylamino, nitro;

optionally substituted (di)heteroaryl($C_1$-$C_4$)alkyl or triheteroaryl($C_1$-$C_4$)alkyl, the heteroaryl group in particular being, cationic or noncationic, 5- or 6-membered monocyclic comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom, such as (tri)(di)halo($C_1$-$C_4$)alkyl such as 2,2,2-trichloroethyl or a group chosen from:
($C_1$-$C_4$)alkyl such as methyl;
($C_1$-$C_4$)alkoxy;
optionally substituted aryl such as phenyl optionally substituted with one or more groups, for instance ($C_1$-$C_4$)alkyl, ($C_1$-$C_4$)alkoxy or hydroxyl;
optionally substituted heteroaryl such as thiophenyl, furanyl, pyrrolyl, pyranyl or pyridyl, optionally substituted with a ($C_1$-$C_4$)alkyl group;
$P(Z^1)R^{\prime 1}R^{\prime 2}R^{\prime 3}$ with $R^{\prime 1}$ and $R^{\prime 2}$, which may be identical or different, representing a hydroxyl, ($C_1$-$C_4$) alkoxy or alkyl group, $R^{\prime 3}$ representing a hydroxyl or ($C_1$-$C_4$)alkoxy group, and $Z^1$ representing an oxygen or sulfur atom
($C_2$-$C_6$)alkylene, in particular allyl $H_2C=CH-CH_2-$;
optionally substituted arylsulfonyl such as p-toluenesulfonyl (Tos);
sterically hindered cycloalkyl such as the adamantyl group;
sterically hindered cycloalkyloxy(thio)carbonyl such as 1-adamantyloxycarbonyl (Adoc) or 1-(adamantyl)-1-methylethoxycarbonyl (Adpoc);
optionally substituted ($C_1$-$C_4$)alkoxy($C_1$-$C_4$)alkyl such as methoxymethyl (MOM), ethoxyethyl (EOM) and isobutoxymethyl;
(tri)(di)halo($C_1$-$C_4$)alkyl such as 2,2,2-trichloroethyl;
$R_eR_fR_gSi$— with $R_e$, $R_f$, and $R_g$, which may be identical or different, representing a ($C_1$-$C_6$)alkyl group, optionally substituted aryl group, optionally substituted (di)aryl($C_1$-$C_4$)alkyl group, optionally substituted triaryl($C_1$-$C_4$)alkyl group, such as benzyl, in particular chosen from trimethylsilyl or TMS, triethylsilyl, isopropyldimethylsilyl, tert-butyldimethylsilyl or TBDMS, (triphenylmethyl)dimethylsilyl, t-butyldiphenylsilyl, methyldiisopropylsilyl, methyl (di-t-butyl)silyl, tribenzylsilyl, tri-p-xylylsilyl, triisopropylsilyl, triphenylsilyl;
or else two contiguous hydroxyl groups can be protected with an alkylene group *—C($R^1$)($R^m$)—(C($R^k$)($R^j$))$_q$—* as drawn below:

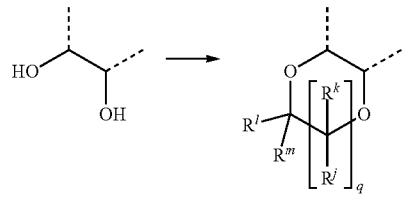

with $R^j$, $R^k$, $R^l$, and $R^m$, which may be identical or different, representing a hydrogen atom or a ($C_1$-$C_4$) alkyl, (poly)halo($C_1$-$C_4$)alkyl, optionally substituted aryl such as phenyl, aryl($C_1$-$C_4$)alkyl such as benzyl, (Poly)halo($C_1$-$C_4$)alkoxy, ($C_1$-$C_4$)alkoxy, halogen, (di)($C_1$-$C_4$)(alkyl)amino or hydroxyl group, or else two $R^j$ and $R^k$ and/or $R^l$, and $R^m$ groups form, together with the carbon atom which bears them, an oxo group or a (hetero)cycloalkyl group such as cyclohexyl or cyclopropyl; q is 0, 1, 2 or 3, preferably *—C($R^l$)($R^m$)—(C($R^k$)($R^j$))$_q$—* represents a methylene, ethylene, propylene, dimethylmethylene, *—C(CH$_3$)$_2$—* or diphenylmethylene *—C(Ph)$_2$-*, cyclopentylidene, cyclohexylidene, cycloheptylidene, benzylidene, pmethoxybenzylidene, 2,4-dimethoxybenzylidene, methoxymethylene and ethoxymethylene;

the term "hydrogen peroxide-generating system" is intended to mean a chemical compound which is not $H_2O_2$ but which can generate hydrogen peroxide and/or which contains hydrogen peroxide, such as a) urea peroxide; b) polymeric complexes that can release hydrogen peroxide, such as polyvinylpyrrolidone/$H_2O_2$, in particular which is in the form of powders, and the other polymeric complexes described in U.S. Pat. Nos. 5,008,093, 3,376,110 and 5,183,901; c) oxidases in the presence of an appropriate substrate (for example glucose in the case of glucose oxidase or uric acid with uricase); d) metal peroxides which, in water, generate hydrogen peroxide, such as calcium peroxide or magnesium peroxide; e) perborates; or f) percarborates; in particular, they are chosen from a) urea peroxide; b) polymeric complexes that can release hydrogen peroxide, chosen from polyvinylpyrrolidone/$H_2O_2$; c) oxidases; e) perborates and f) percarborates.

According to one particular embodiment of the invention, the compounds of formula (I) are such that, taken together or separately, R' represents a hydrogen atom and/or R represents a hydroxyl group or an amino group N(H)—R'$_1$ with R'$_1$ representing a $C_1$-$C_{16}$ alkyl group, preferably methyl, n-propyl, n-hexyl, n-tetradecyl and/or X represents an oxygen atom.

It is understood that, for the compounds of formula (I) as defined above, when S* represents a monosaccharide radical, then it can be in pyranose form (the sugar heterocycle which constitutes it comprises 6 ring members) or furanose form (the sugar heterocycle which constitutes it comprises 5 ring members); and when S* represents a polysaccharide radical, it comprises the sequence of 2 to 5 saccharide units, which may be identical to or different from one another, which may be in furanose or pyranose form. Preferably, the polysaccharide is a disaccharide which results from the sequence of a saccharide unit in furanose form and a unit in pyranose form or the sequence of a saccharide unit in pyranose form and a unit in furanose form; whether it is for the monosaccharide or polysaccharide radical, each saccharide unit may be in levorotatory L or dextrorotatory D form, and α or β anomeric form.

According to one preferred embodiment, the sugar radical S* represents a monosaccharide radical in which the heterocycle constituting it contains 4 or 5 carbon atoms, of formula S*' below:

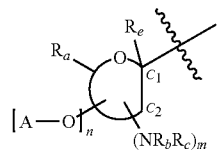

$R_a$ representing a hydrogen atom, a ($C_1$-$C_4$)alkyl group such as methyl or a (poly)hydroxy($C_1$-$C_4$)alkyl group such as hydroxymethyl or 1,2-dihydroxyethyl, the hydroxyl function(s) of the (poly)hydroxy($C_1$-$C_4$)alkyl group being substituted with A as defined hereinafter—;

it being understood that the $R_a$ radical is in the $C_5$ position if the sugar unit is in pyranose form or in the $C_4$ position if it is in furanose form;

$R_b$ represents a hydrogen atom or a ($C_1$-$C_4$)alkyl group, preferably hydrogen;

$R_c$ representing a hydrogen atom, or a protective group for the amine function, such as $R_d$—C(X')—, identical in the case of several hydroxyl functions, with X' representing an oxygen or sulfur atom, in particular an oxygen atom, and $R_d$ representing a ($C_1$-$C_4$)alkyl group, R, preferably representing an acetyl group $CH_3$—C(O)—;

$R_e$ represents a hydrogen atom or a $CH_2$—O-A group;

A representing a hydrogen atom, a ($C_1$-$C_6$)alkyl group or a hydroxyl-function-protecting group, such as $R_d$—C(X')— as defined above and in particular acetyl $CH_3$—C(O)—, or else, when n is greater than or equal to 2 and two groups A-O are contiguous, then two A groups can together form a linear or branched ($C_1$-$C_6$)alkylene chain;

preferably, all the protective groups for A are identical;

n is equal to 1, 2 or 3 and m is equal to 0 or 1.

According to another preferred embodiment, the sugar radical S* represents a polysaccharide radical constituted of 2 to 5 saccharide units, in particular of 2 to 3 and preferably of 2 saccharide units, linked together via an oxygen atom (oxy), 1→4 ($C_1$ of one saccharide unit→$C_4$ of the other saccharide unit) or 1→3 ($C_1$ of one saccharide unit→$C_3$ of the other saccharide unit) or 1→6 ($C_1$ of one saccharide unit→$C_6$ of the other saccharide unit), each saccharide unit of which is constituted of a heterocycle comprising 4 or 5 carbon atoms, of formula S*" below:

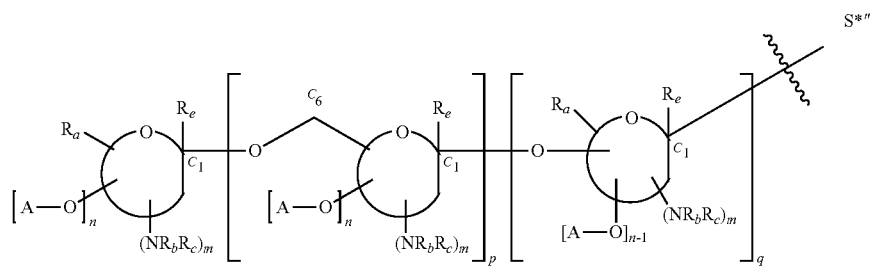

in which formula S*", p and q represent integers of inclusively between 0 and 4 with p+q inclusively between 1 and 4, particularly between 1 and 2, preferentially p+q=1;

$R_a$, which may be identical or different, are as defined above, $R_b$, which may be identical or different, are as defined above, $R_c$, which may be identical or different, are as defined above, $R_e$, which may be identical or different, are as defined above, A, which may be identical or different, are as defined above, m, which may be identical or different, are as defined above, n, which may be identical or different, are as defined above, it being understood that the two sugar units between the square brackets q and p can interchange, i.e. can represent the chain below:

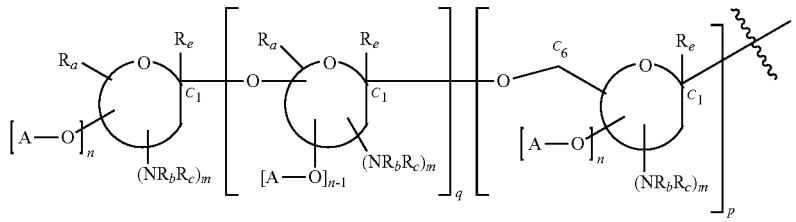

According to one preferred variant of the invention, the compounds of formula (I) are such that:
S* represents a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;
said radical S* comprising one or more radicals —$OR_s$ and optionally one or two radicals —$NHR'_s$,
said monosaccharide or disaccharide radical being connected to the rest of the molecule by a bond between the $C^1$ carbon atom of the sugar or one of the sugars and this bond possibly being α or β anomeric;
X represents an oxygen atom or a sulfur atom, preferably an oxygen atom;
R' represents:
i) a hydrogen atom;
ii) a $(C_1-C_{18})$alkyl group, preferably $(C_1-C_6)$alkyl group such as methyl;
iii) a $(C_1-C_{18})$alkenyl radical, preferably $(C_1-C_6)$alkenyl radical, such as prenyl;
iv) an aryl$(C_1-C_4)$alkyl radical optionally substituted in particular with at least one hydroxyl and/or saturated or unsaturated $(C_1-C_4)$alkoxy group, in particular an aryl $(C_1-C_4)$alkyl radical such as benzyl;
v) or a $(C_1-C_{18})$alkylcarbonyl, preferably $(C_1-C_6)$alkylcarbonyl radical, in particular acetyl ($CH_3$—CO—);
R represents a group chosen from:
i) hydroxyl;
ii) saturated or unsaturated $(C_1-C_{18})$alkoxy, which is preferably saturated and more preferentially saturated $C_1-C_6$, such as methoxy, ethoxy, isopropyloxy or tert-butyloxy;
iii) optionally substituted aryl$(C_1-C_6)$alkoxy, such as benzyloxy;
iv) amino $NR_1R_2$ with $R_1$ and $R_2$ independently denoting a hydrogen atom, a $(C_1-C_{16})$alkyl radical such as methyl, n-propyl, n-hexyl or n-tetradecyl, a $(C_2-C_{16})$ alkenyl radical, an aryl radical such as phenyl, or an aryl$(C_1-C_4)$alkyl group which is optionally substituted in particular with at least one hydroxyl and/or saturated or unsaturated $(C_1-C_4)$alkoxy group, such as benzyl;
$R_s$ represents a hydrogen atom or a radical chosen from the radicals: a) methoxymethyl; b) (phenyldimethylsilyl)methoxyphenyl; c) benzyloxymethyl; d) p-methoxybenzyloxymethyl; e) (4-methoxyphenoxy)methyl; f) t-butoxymethyl; g) tetrahydropyranyl; h) tetrahydrofuranyl; i) 2-trimethylsilylethyl; j) t-butyl; k) p-methoxyphenyl; l) p-methoxybenzyl; m) trimethylsilyl; n) triethylsilyl; o) dimethylisopropylsilyl; p) t-butyldimethylsilyl; q) acetyl; r) trifluoroacetyl; s) adamantyl; t) benzoyl; and u) FMOC,
said radicals $R_s$ preferably all being identical and all preferably denoting a hydrogen atom or an acetyl radical;
$R'_s$ represents a radical chosen from a hydrogen atom or an acetyl radical.

Preferably, the compounds (I) as defined above are such that:
when S* represents a glucose and R' represents a hydrogen atom, then R is other than a —O-$^t$Bu group; and
when S* represents a mannose and R' represents a hydrogen atom, then R is other than a diethylamino group $N(Et)_2$.

According to a more preferred variant of the invention, the compounds of formula (I) are such that:
S* denotes a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;
said radical S* comprising one or more radicals —$OR_s$ and optionally one or two radicals $NHR'_s$;
said monosaccharide or disaccharide radical being connected to the rest of the molecule by a bond between the $C^1$ carbon atom of the sugar or one of the sugars and this bond possibly being α or β anomeric;
X denotes an oxygen atom;
R' denotes
i) a hydrogen atom;
ii) a $(C_1-C_{18})$alkyl group, preferably $(C_1-C_6)$alkyl group such as methyl;
iii) a $(C_1-C_{18})$alkenyl radical, preferably $(C_1-C_6)$alkenyl radical, such as prenyl;
iv) an optionally substituted aryl$(C_1-C_4)$alkyl radical, in particular an aryl$(C_1-C_4)$alkyl radical such as benzyl;
v) or a $(C_1-C_{18})$alkylcarbonyl, preferably $(C_1-C_6)$alkylcarbonyl radical, in particular acetyl ($CH_3$—CO—);
R denotes a group chosen from:
i) hydroxyl;
ii) saturated or unsaturated $(C_1-C_{18})$alkoxy, which is preferably saturated and more preferentially saturated $C_1-C_6$, such as methoxy, ethoxy, isopropyloxy or tert-butyloxy;

iii) aryl($C_1$-$C_6$)alkoxy optionally substituted in particular with at least one hydroxyl and/or saturated or unsaturated ($C_1$-$C_4$)alkoxy group such as benzyloxy;

iv) amino $NR_1R_2$ with $R_1$ and $R_2$ independently denoting a hydrogen atom, a ($C_1$-$C_{16}$)alkyl radical such as methyl, n-propyl, n-hexyl or n-tetradecyl, a ($C_2$-$C_{16}$) alkenyl radical, an aryl radical such as phenyl, or an aryl($C_1$-$C_4$)alkyl group which is optionally substituted in particular with at least one hydroxyl and/or saturated or unsaturated ($C_1$-$C_4$)alkoxy group such as benzyl;

$R_s$ denotes a hydrogen atom or an acetyl radical, said radicals $R_s$ all being identical;

$R'_s$ denotes a radical chosen from a hydrogen atom or an acetyl radical.

Preferably, the compounds (I) as defined above are such that:

when S* represents a glucose and R' represents a hydrogen atom, then R is other than a —O-$^t$Bu group; and when S* represents a mannose and R' represents a hydrogen atom, then R is other than a diethylamino group $N(Et)_2$.

More preferentially, the compounds of formula (I) are chosen from the compounds of formulae (I'), (I''), (I'''), (I'a), (I''a) and (I''''a) below:

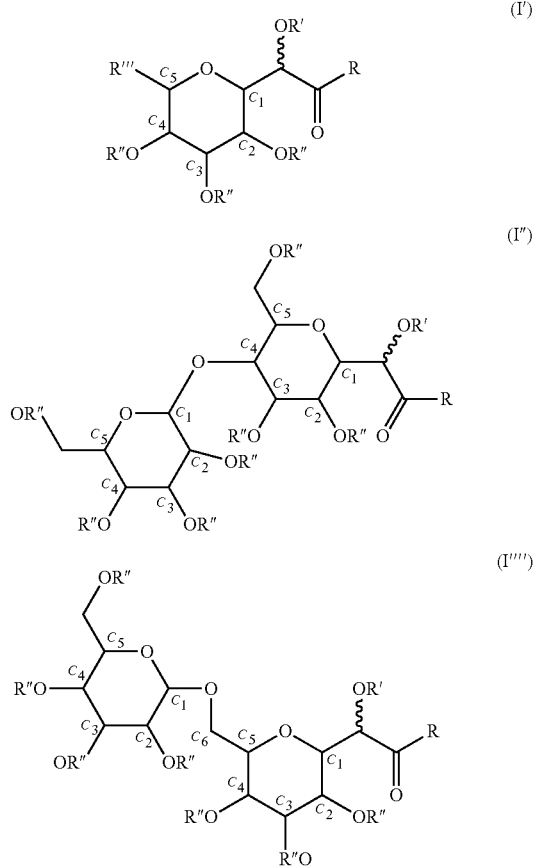

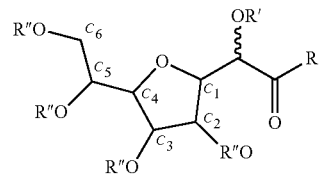

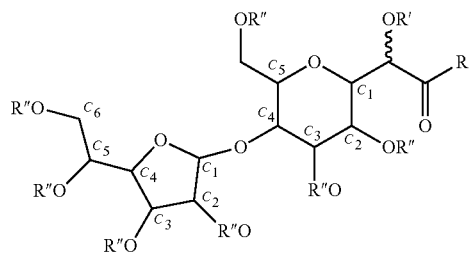

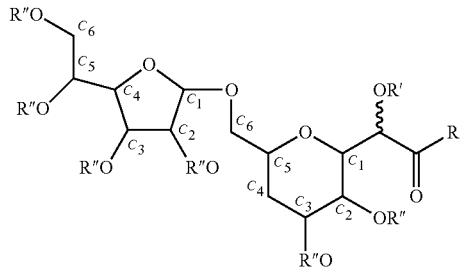

and also the solvates thereof such as hydrates, the optical and geometric isomers and tautomers thereof and the organic or mineral base or acid salts thereof, in which formulae (I'), (I''), (I''''), (I'a), (I''a) and (I''''a):

R is as defined below, and preferably represents one of the following groups: hydroxyl;

$O^-$, $M^-$ with $M^+$ representing a cationic counterion such as the metal Zinc ($Zn^{2+}$), manganese ($Mn^{2+}$), copper ($Cu^{2+}$), iron, an alkali metal ($Na^+$, $K^+$) or alkaline-earth metal, or ammonium; optionally unsaturated ($C_1$-$C_6$)alkoxy; amino —$NR_1R_2$ with $R_1$ and $R_2$, which may be identical or different, representing a hydrogen atom, ($C_1$-$C_{18}$)alkyl; preferably $C_1$-$C_{16}$ alkyl such as methyl, n-propyl, n-hexyl, or n-tetradecyl (n-$C_{14}$);

R' is as defined above, and preferably represents a hydrogen atom or an acetyl radical, and preferably a hydrogen atom;

R'' is as defined above, and preferably represents a hydrogen atom or an acetyl radical, and preferably a hydrogen atom;

R''' represents a hydrogen atom, or a ($C_1$-$C_6$)alkyl group, or a —$CH_2OR''$ group with R'' as defined above, in particular hydrogen or an acetyl radical, and preferably a hydrogen atom.

According to one particular embodiment, the compounds of the invention are of formula (I'). According to another particular embodiment of the invention, the compounds of the invention are of formula (I''). According to another particular embodiment of the invention, the compounds of the invention are of formula (I'''').

According to another particular embodiment of the invention, the compounds of the invention are of formula (I'a).

According to another particular embodiment of the invention, the compounds of the invention are of formula (I''a). According to another particular embodiment of the invention, the compounds of the invention are of formula (I'''a).

According to one particular embodiment, S* and S*' represent a monosaccharide chosen from glucose, galactose, mannose, xylose, lyxose, fucose, arabinose, rhamnose, ribose, deoxyribose, quinovose, fructose, sorbose, talose, threose, erythrose, N-acetylglucosamine, N-acetylgalactosamine, glucosamine and galactosamine.

In particular, S* and S*' represent a monosaccharide chosen from D-glucose, D-galactose, D-mannose, D-xylose, L-xylose, D-lyxose, L-lyxose, L-fucose, L-arabinose, D-arabinose, L-rhamnose, L-ribose, D-ribose, 2-deoxy-D-ribose, 2-deoxy-L-ribose, D-quinovose, D-fructose, L-sorbose, D-talose, D-threose, D-erythrose, L-threose, L-erythrose, N-acetyl-D-glucosamine, N-acetyl-D-galactosamine, D-glucosamine and D-galactosamine. Preferably, S denotes a monosaccharide chosen from D-glucose, D-galactose, D-mannose, D-xylose, D-lyxose, L-fucose, L-arabinose, L-rhamnose, D-ribose, 2-deoxy-D-ribose, D-quinovose, D-fructose, L-sorbose, D-talose, D-threose, D-erythrose, N-acetyl-D-glucosamine, N-acetyl-D-galactosamine, D-glucosamine and D-galactosamine.

Advantageously, S* and S'' represent a monosaccharide chosen from glucose, xylose, rhamnose, mannose and galactose or a disaccharide chosen from lactose, maltose and cellobiose. In particular, S* denotes a monosaccharide chosen from D-glucose, D-xylose, L-rhamnose, D-mannose and D-galactose or a disaccharide chosen from D-lactose, D-maltose and D-cellobiose.

Preferably, S* and S*' represent a sugar chosen from glucose, xylose and lactose. More particularly, S* and S*' denote a sugar chosen from D-glucose, L-xylose and D-lactose. Preferentially, S* and S*' denote glucose or xylose. In particular, S* and S*' denote D-glucose or D-xylose.

More preferentially, S* and S*' denote glucose. In particular, S* and S*' denote D-glucose.

According to another particular embodiment, S* and S*''' represent a polysaccharide and in particular a disaccharide chosen from lactose, maltulose, palatinose, lactulose, amygdalose, turanose, cellobiose, isomaltose, rutinose and maltose.

According to one particular embodiment, the radicals S* and S*''' represent a polysaccharide and in particular a disaccharide chosen from D-lactose, maltulose, palatinose, lactulose, amygdalose, D-turanose, D-cellobiose, isomaltose, rutinose and D-maltose.

According to one particular embodiment, R preferably represents a group $N(H)R_1$ and more particularly $N(H)CH_3$.

According to one particular embodiment of the invention, the compounds of formula (I) are such that R represents an amino group $—NR_1R_2$ with $R_1$ and $R_2$, which may be identical or different, representing a hydrogen atom, aryl such as phenyl, a linear or branched aryl($C_1$-$C_4$)alkyl group such as benzyl, a linear or branched ($C_1$-$C_{18}$)alkyl group, a ($C_2$-$C_{18}$)alkenyl group, or a ($C_2$-$C_{18}$)alkynyl group; preferably a $C_1$-$C_{16}$ alkyl group such as methyl, n-propyl, n-hexyl, or n-tetradecyl (n-$C_{14}$).

According to one embodiment of the invention, the compounds (I) are compounds of formula (Ia) (amide compounds):

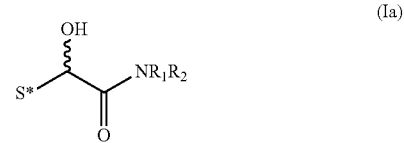

(Ia)

and also the solvates thereof such as hydrates, the optical and geometric isomers and tautomers thereof and the organic or mineral base or acid salts thereof, in which formula (Ia), S*, $R_1$ and $R_2$ are as defined above.

Preferably, S* denotes a sugar chosen from glucose, xylose, rhamnose, mannose, galactose and lactose. More particularly, S denotes a sugar chosen from D-glucose, D-xylose, L-rhamnose, D-mannose, D-galactose and D-lactose.

Preferably, $R_1$ represents a hydrogen atom; and $R_2$ represents a benzyl radical or a linear or branched, saturated or unsaturated $C_1$-$C_{18}$, preferably $C_1$-$C_{16}$, alkyl radical such as methyl, n-propyl, n-hexyl or n-tetradecyl.

More preferentially, $R_1$ represents a hydrogen atom; and $R_2$ represents a linear or branched $C_1$-$C_5$ alkyl radical such as methyl, ethyl, n-propyl, n-butyl or n-pentyl.

In particular, S* denotes a sugar chosen from glucose, xylose, rhamnose, mannose, galactose and lactose; $R_1$ represents a hydrogen atom; and $R_2$ denotes a linear or branched $C_1$-$C_{18}$ alkyl radical; more particularly, $R_2$ denotes a linear or branched $C_1$-$C_{16}$, alkyl radical; preferentially, $R_2$ denotes a radical chosen from methyl, n-propyl, n-hexyl and n-tetradecyl.

More particularly, S* denotes a sugar chosen from glucose, xylose, rhamnose, mannose, galactose and lactose; $R_1$ represents a hydrogen atom; and $R_2$ represents a linear or branched $C_1$-$C_5$ alkyl radical such as methyl, ethyl, n-propyl, n-butyl or n-pentyl.

Preferentially, S* denotes a sugar chosen from glucose; $R_1$ represents a hydrogen atom; and $R_2$ denotes a linear or branched $C_1$-$C_{18}$ alkyl radical; more particularly, $R_2$ denotes a linear or branched $C_1$-$C_{16}$, alkyl radical; preferentially, $R_2$ denotes a radical chosen from methyl, n-propyl, n-hexyl and tetradecyl.

More preferentially, S* denotes a sugar chosen from glucose; $R_1$ represents a hydrogen atom; and $R_2$ represents a linear or branched $C_1$-$C_5$ alkyl radical such as methyl, ethyl, n-propyl, n-butyl or n-pentyl.

For the compounds (Ia) described above, $R_2$ preferably represents a methyl or propyl radical and preferentially a methyl radical.

As examples of compounds of formula (Ia), mention may in particular be made of the following compounds:

| Compound | S* = D-Glucose |
|---|---|
| 1 | 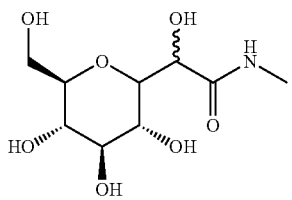 [SMILES: CNC(=O)C(O)C1O[C@H](CO)[C@@H](O)[C@H](O)[C@H]1O] |
| 2 | 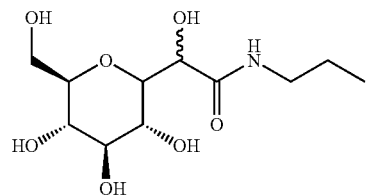 [SMILES: CCCNC(=O)C(O)C1O[C@H](CO)[C@@H](O)[C@H](O)[C@H]1O] |
| 3 | 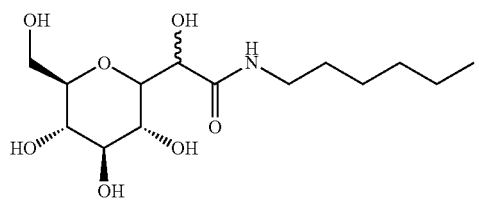 [SMILES: CCCCCCNC(=O)C(O)C1O[C@H](CO)[C@@H](O)[C@H](O)[C@H]1O] |
| 4 | 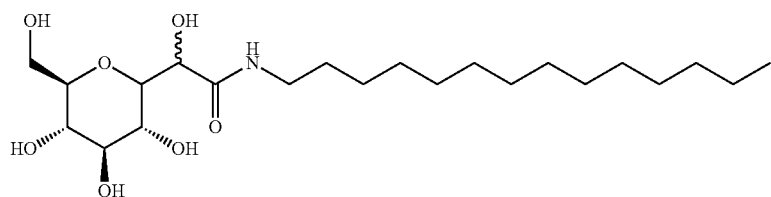 [SMILES: CCCCCCCCCCCCCCNC(=O)C(O)C1O[C@H](CO)[C@@H](O)[C@H](O)[C@H]1O] |
| Compound | S* = L-Xylose |
|---|---|
| 5 | 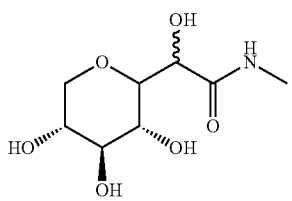 |
| 6 | 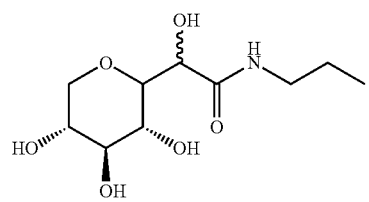 [SMILES: CCCNC(=O)C(O)C1OC[C@@H](O)[C@H](O)[C@H]1O] |
| 7 | 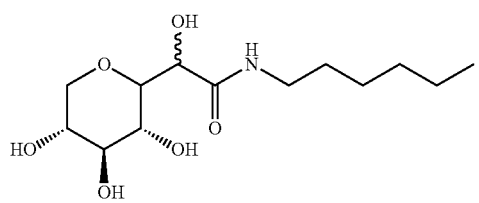 [SMILES: CCCCCCNC(=O)C(O)C1OC[C@@H](O)[C@H](O)[C@H]1O] |

-continued
| | |
|---|---|
| 8 | 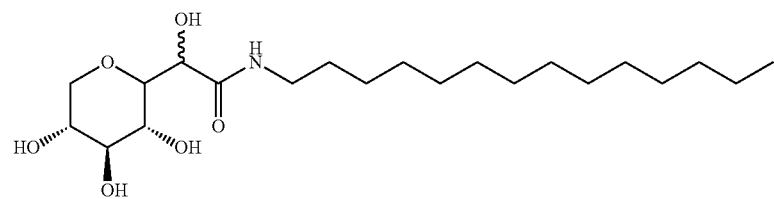 [SMILES: CCCCCCCCCCCCCCNC(=O)C(O)C1OC[C@@H](O)[C@H](O)[C@H]1O] |
| Compound | S* = L-Rhamnose |
| 9 | 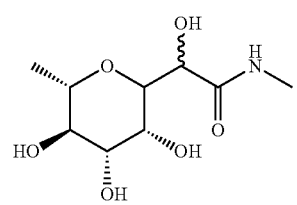 [SMILES: CNC(=O)C(O)C1O[C@@H](C)[C@H](O)[C@@H](O)[C@H]1O] |
| 10 | 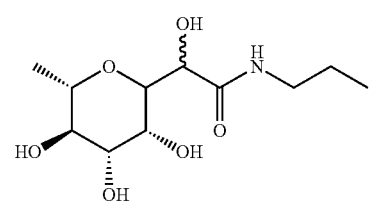 [SMILES: CCCNC(=O)C(O)C1O[C@@H](C)[C@H](O)[C@@H](O)[C@H]1O] |
| 11 | 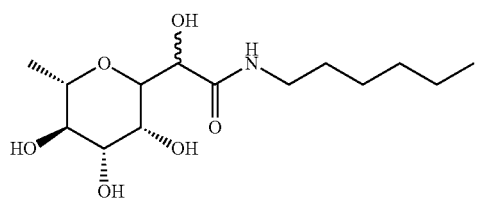 [SMILES: CCCCCCNC(=O)C(O)C1O[C@@H](C)[C@H](O)[C@@H](O)[C@H]1O] |
| 12 | 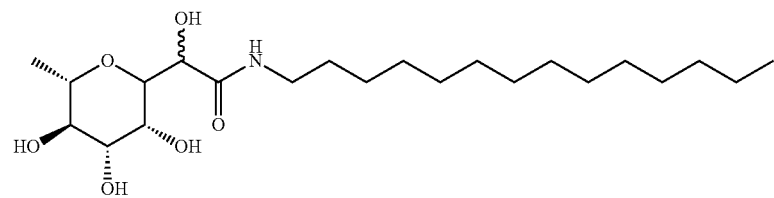 [SMILES: CCCCCCCCCCCCCCNC(=O)C(O)C1O[C@@H](C)[C@H](O)[C@@H](O)[C@H]1O] |
| Compound | S* = D-mannose |
| 13 | 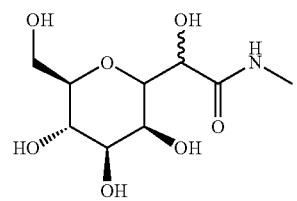 [SMILES: CNC(=O)C(O)C1O[C@H](CO)[C@@H](O)[C@H](O)[C@@H]1O] |
| 14 | 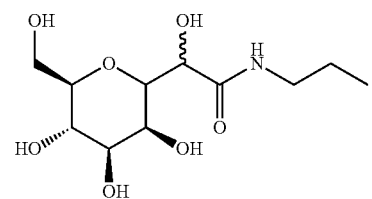 [SMILES: CCCNC(=O)C(O)C1O[C@H](CO)[C@@H](O)[C@H](O)[C@@H]1O] |

-continued
| | |
|---|---|
| 15 | 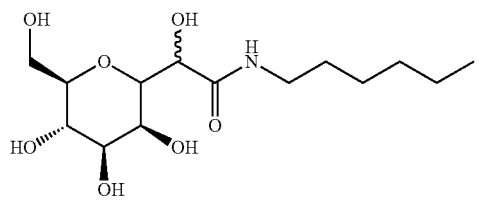 [SMILES: CCCCCCNC(=O)C(O)C1O[C@H](CO)[C@@H](O)[C@H](O)[C@@H]1O] |
| 16 | 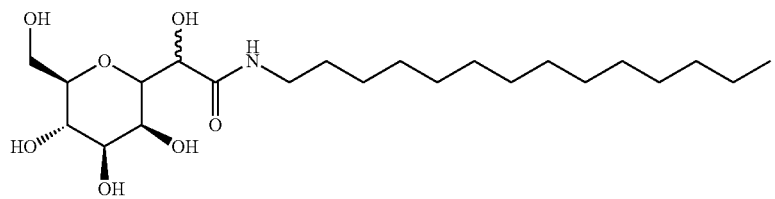 [SMILES: CCCCCCCCCCCCCCNC(=O)C(O)C1O[C@H](CO)[C@@H](O)[C@H](O)[C@@H]1O] |
| Compound | S* = D-galactose |
|---|---|
| 17 | 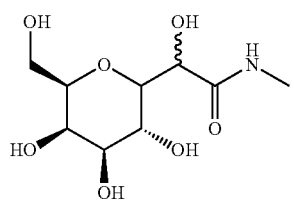 [SMILES: CNC(=O)C(O)C1O[C@H](CO)[C@H](O)[C@H](O)[C@H]1O] |
| 18 | 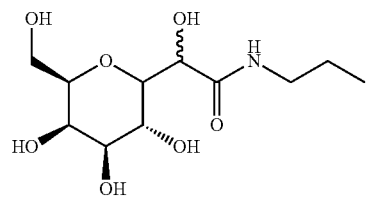 [SMILES: CCCNC(=O)C(O)C1O[C@H](CO)[C@H](O)[C@H](O)[C@H]1O] |
| 19 | 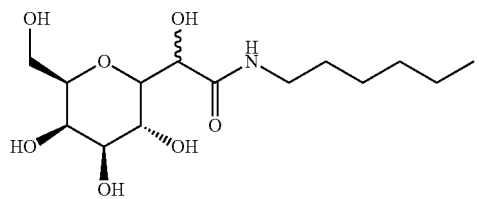 [SMILES: CCCCCCNC(=O)C(O)C1O[C@H](CO)[C@H](O)[C@H](O)[C@H]1O] |
| 20 | 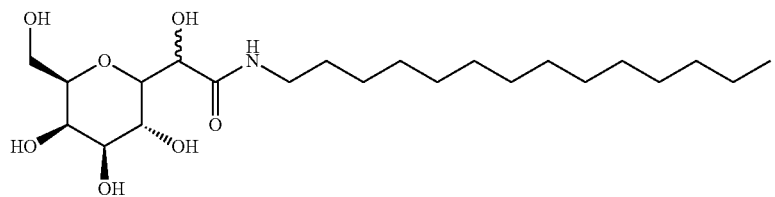 [SMILES: CCCCCCCCCCCCCCNC(=O)C(O)C1O[C@H](CO)[C@H](O)[C@H](O)[C@H]1O] |
| Compound | S* = D-lactose |
|---|---|
| 21 | 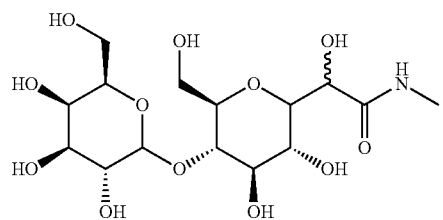 [SMILES: CNC(=O)C(O)C1O[C@H](CO)[C@@H](OC2O[C@H](CO)[C@H](O)[C@H](O)[C@H]2O)[C@H](O)[C@H]1O] |

22

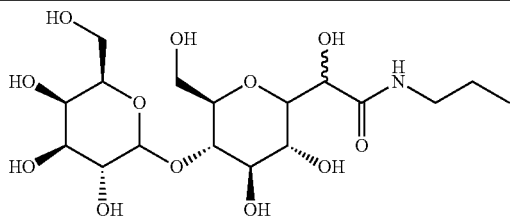

23

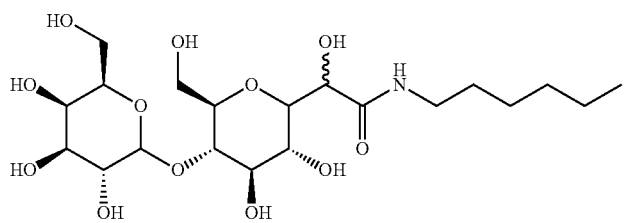 [SMILES: CCCCCCNC(=O)C(O)C1O[C@H](CO)[C@@H](OC2O[C@H](CO)[C@H](O)[C@H](O)[C@H]2O)[C@H](O)[C@H]1O]

24

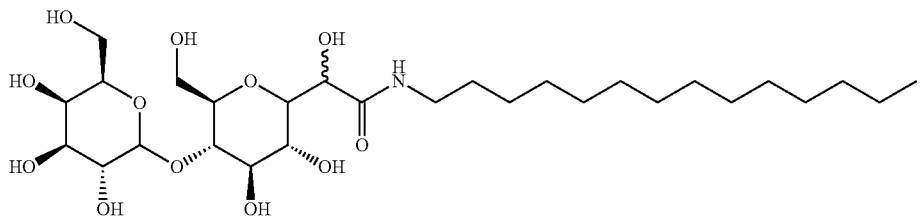 [SMILES: CCCCCCCCCCCCCCNC(=O)C(O)C1O[C@H](CO)[C@@H](OC2O[C@H](CO)[C@H](O)[C@H](O)[C@H]2O)[C@H](O)[C@H]1O]

and also the solvates thereof such as hydrates, and the organic or mineral base or acid salts thereof.

The compounds 1, 2, 5, 6, 9, 10, 13, 14, 17, 18, 21 and 22 described above are particularly preferred.

As examples of compounds of formula (Ia), mention may also be made of the compounds 1 to 24 in which the hydroxyl radicals of the sugar are substituted with a group chosen from acetyl, THP, TMS, TBDMS, tosyl, tert-butyl, MOM and benzoate, in particular substituted with the same group. According to another variant, as examples of compounds of sugar formula (Ia), mention may be made of the compounds 1 to 24 in which the hydroxyl radicals of the sucre are substituted with an acetyl radical.

According to a second embodiment, the compounds (I) are compounds of formula (Ib) (ester compounds):

(Ib)

and also the solvates thereof such as hydrates, the optical and geometric isomers and tautomers thereof and the organic or mineral base or acid salts thereof, in which formula (Ib):

S* is as defined above:

R" denotes a $(C_1-C_{18})$alkyl, $(C_2-C_{18})$alkenyl or $(C_2-C_{18})$ alkynyl radical, preferably a $(C_1-C_6)$alkyl radical, such as ethyl, isopropyl, n-hexyl or prenyl; an aryl radical such as phenyl, or an aryl$(C_1-C_6)$alkyl radical such as benzyl.

Preferably, S* denotes a sugar chosen from glucose, xylose, rhamnose, mannose, galactose and lactose. More particularly, S denotes a sugar chosen from D-glucose, D-xylose, L-rhamnose, D-mannose, D-galactose and D-lactose. Preferentially, S denotes a sugar chosen from glucose or xylose.

In particular, the compounds of formula (Ib) are such that R" denotes a $C_1-C_4$ alkyl radical, in particular methyl or ethyl, and S* denotes a sugar chosen from glucose, xylose, rhamnose, mannose, galactose and lactose; more particularly, S* denotes a sugar chosen from glucose and xylose, preferentially D-glucose and D-xylose.

As examples of compounds of formula (Ib), mention may in particular be made of the following compounds:

| Compound | S* = D glucose |
|---|---|
| 25 | 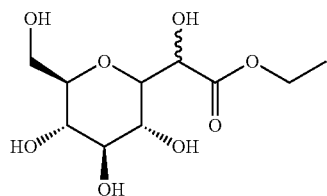 [SMILES: CCOC(=O)C(O)C1O[C@H](CO)[C@@H](O)[C@H](O)[C@H]1O] |
| 26 | 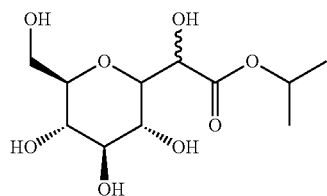 [SMILES: CC(C)OC(=O)C(O)C1O[C@H](CO)[C@@H](O)[C@H](O)[C@H]1O] |
| 27 | 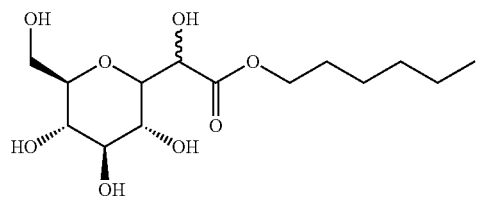 [SMILES: CCCCCCOC(=O)C(O)C1O[C@H](CO)[C@@H](O)[C@H](O)[C@H]1O] |
| 28 | 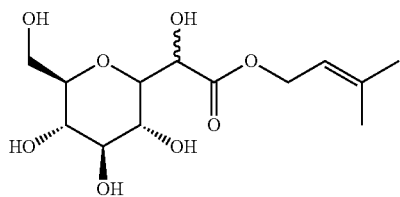 [SMILES: CC(C)=CCOC(=O)C(O)C1O[C@H](CO)[C@@H](O)[C@H](O)[C@H]1O] |
| Compound | S* = D xylose |
|---|---|
| 29 | 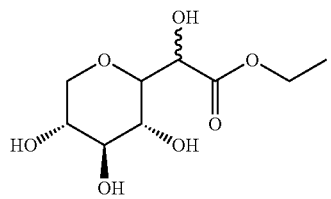 [SMILES: CCOC(=O)C(O)C1OC[C@@H](O)[C@H](O)[C@H]1O] |
| 30 | 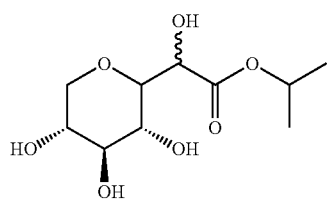 [SMILES: CC(C)OC(=O)C(O)C1OC[C@@H](O)[C@H](O)[C@H]1O] |
| 31 | 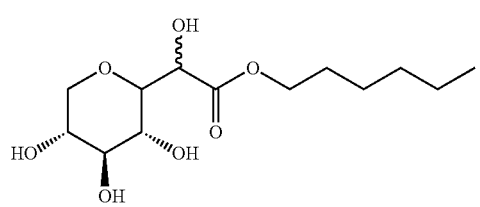 [SMILES: CCCCCCOC(=O)C(O)C1OC[C@@H](O)[C@H](O)[C@H]1O] |

-continued
| 32 | 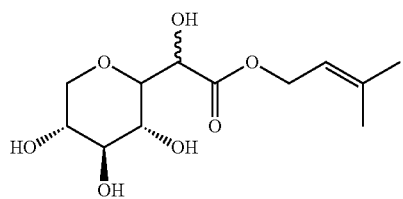 [SMILES: CC(C)=CCOC(=O)C(O)C1OC[C@@H](O)[C@H](O)[C@H]1O] |
|---|---|
| Compound | S* = L-Rhamnose |
| 33 | 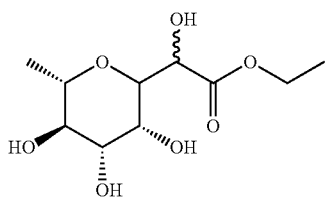 [SMILES: CCOC(=O)C(O)C1O[C@@H](C)[C@H](O)[C@@H](O)[C@H]1O] |
| 34 | 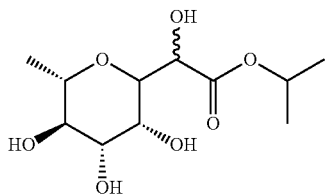 [SMILES: CC(C)OC(=O)C(O)C1O[C@@H](C)[C@H](O)[C@@H](O)[C@H]1O] |
| 35 | 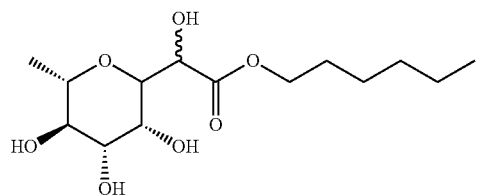 [SMILES: CCCCCCOC(=O)C(O)C1O[C@@H](C)[C@H](O)[C@@H](O)[C@H]1O] |
| 36 | 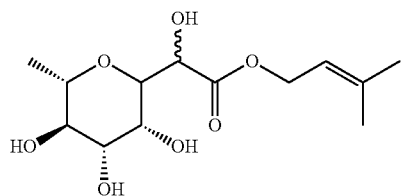 [SMILES: CC(C)=CCOC(=O)C(O)C1O[C@@H](C)[C@H](O)[C@@H](O)[C@H]1O] |
| Compound | S* = D-mannose |
| 37 | 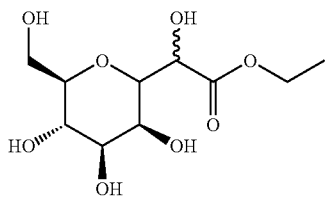 [SMILES: CCOC(=O)C(O)C1O[C@H](CO)[C@@H](O)[C@H](O)[C@@H]1O] |
| 38 | 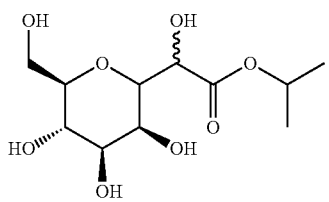 [SMILES: CC(C)OC(=O)C(O)C1O[C@H](CO)[C@@H](O)[C@H](O)[C@@H]1O] |

| | |
|---|---|
| 39 | 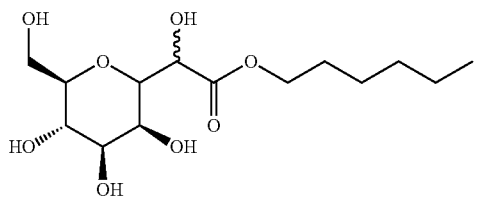 [SMILES: CCCCCCOC(=O)C(O)C1O[C@H](CO)[C@@H](O)[C@H](O)[C@@H]1O] |
| 40 | 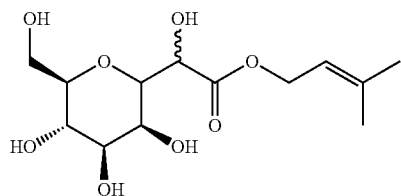 [SMILES: CC(C)=CCOC(=O)C(O)C1O[C@H](CO)[C@@H](O)[C@H](O)[C@@H]1O] |
| Compound | S* = D-galactose |
|---|---|
| 41 | 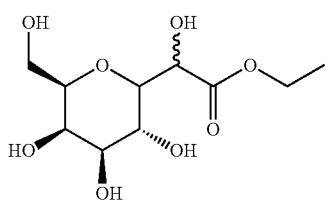 [SMILES: CCOC(=O)C(O)C1O[C@H](CO)[C@H](O)[C@H](O)[C@H]1O] |
| 42 | 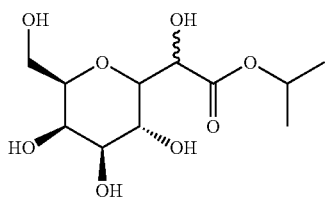 [SMILES: CC(C)OC(=O)C(O)C1O[C@H](CO)[C@H](O)[C@H](O)[C@H]1O] |
| 43 | 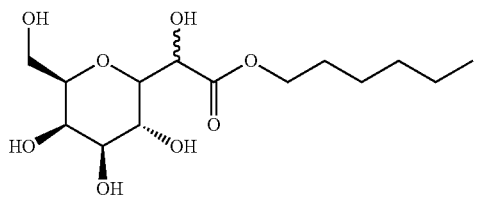 [SMILES: CCCCCCOC(=O)C(O)C1O[C@H](CO)[C@H](O)[C@H](O)[C@H]1O] |
| 44 | 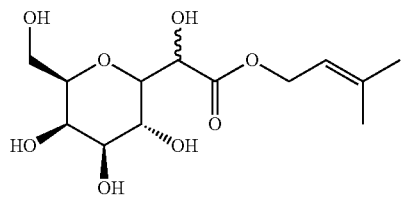 [SMILES: CC(C)=CCOC(=O)C(O)C1O[C@H](CO)[C@H](O)[C@H](O)[C@H]1O] |
| Compound | S* = D-lactose |
|---|---|
| 45 | 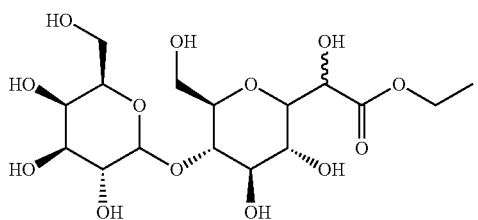 [SMILES: CCOC(=O)C(O)C1O[C@H](CO)[C@@H](OC2O[C@H](CO)[C@H](O)[C@H](O)[C@H]2O)[C@H](O)[C@H]1O] |

46 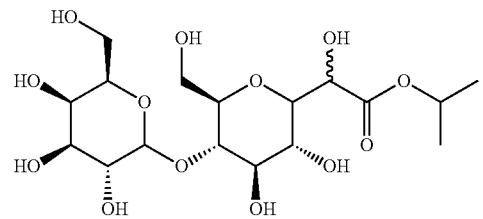 [SMILES: CC(C)OC(=O)C(O)C1O[C@H](CO)[C@@H](OC2O[C@H](CO)[C@H](O)[C@H](O)[C@H]2O)[C@H](O)[C@H]1O]

47 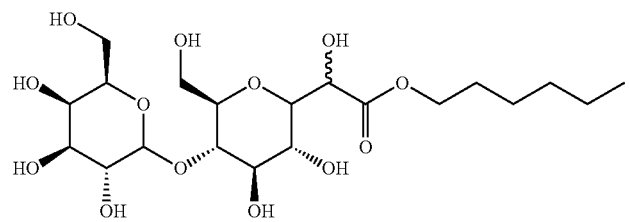 [SMILES: CCCCCCOC(=O)C(O)C1O[C@H](CO)[C@@H](OC2O[C@H](CO)[C@H](O)[C@H](O)[C@H]2O)[C@H](O)[C@H]1O]

48 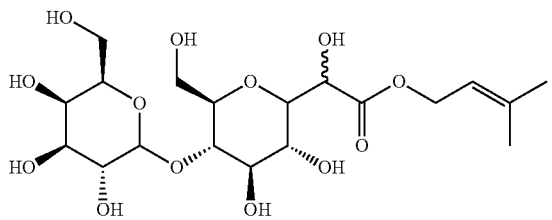 [SMILES: CC(C)=CCOC(=O)C(O)C1O[C@H](CO)[C@@H](OC2O[C@H](CO)[C@H](O)[C@H](O)[C@H]2O)[C@H](O)[C@H]1O]

and also the solvates thereof such as hydrates, and the organic or mineral base or acid salts thereof.

As examples of compounds of formula (Ib), mention may also be made of the compounds 25 to 48 in which all the hydroxyl functions of the sugar are substituted with a group chosen from acetyl, THP, TMS, TBDMS, tosyl, tert-butyl, MOM and benzoate, and in particular all the hydroxyl functions of the sugar are substituted with the same group chosen from the list above. In particular, mention may be made of the compounds 25 to 28 in which all the hydroxyl functions of the sugar are substituted with an acetyl group.

According to a third embodiment of the invention, the compounds (I) are compounds of formula (Ic) (acid compounds):

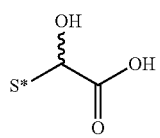
(Ic)

and also the solvates thereof such as hydrates, the optical and geometric isomers and tautomers thereof and the organic or mineral base or acid salts thereof.

Compound of formula (Ic) in which S* is as defined above.

As compound (Ic) mention may be made of the following compounds:

| Compound | S* = D glucose |
|---|---|
| 49 | 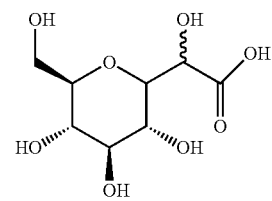 [SMILES: O=C(O)C(O)C1O[C@H](CO)[C@@H](O)[C@H](O)[C@H]1O] |
| | S* = D galactose |
| 50 | 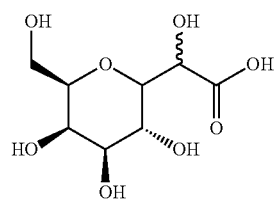 [SMILES: O=C(O)C(O)C1O[C@H](CO)[C@H](O)[C@H](O)[C@H]1O] |
| | S* = D mannose |
| 51 | 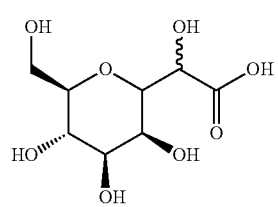 [SMILES: O=C(O)C(O)C1O[C@H](CO)[C@@H](O)[C@H](O)[C@@H]1O] |

-continued

S* = D xylose

52

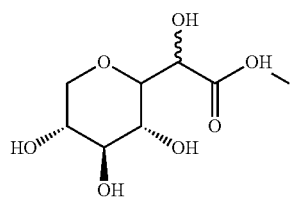

S* = L rhamnose

53

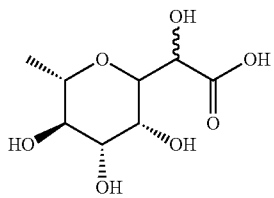

| Compound | S* = D-lactose |
|---|---|
| 54 | 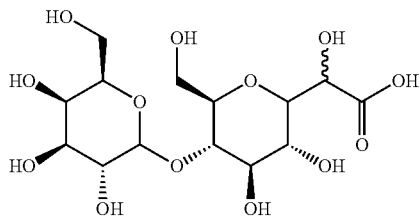 [SMILES: O=C(O)C(O)C1O[C@H](CO)[C@@H](OC2O[C@H](CO)[C@H](O)[C@H](O)[C@H]2O)[C@H](O)[C@H]1O] | and also the solvates thereof such as hydrates, and the organic or mineral base or acid salts thereof.

As examples of compounds of formula (Ic), mention may also be made of the compounds 49 to 54 in which all the hydroxyl groups of the sugar are substituted with a group chosen from acetyl, THP, TMS, TBDMS, trityl, tosyl, tert-butyl, MOM and benzoate, and in particular the compounds 49 to 54 for which all the hydroxyl functions of the sugar are substituted with the same group chosen from the list above. In particular, mention may be made of the compounds 49 to 54 in which all the hydroxyl functions of sugar are substituted with an acetyl group.

The acceptable solvates of the compounds used in the present invention comprise conventional solvates such as those formed during the last step of the preparation of said compounds due to the presence of solvents. Mention may be made, by way of example, of the solvates due to the presence of water (hydrates) or of linear or branched alcohols, such as ethanol or isopropanol.

The salts of the compounds (I) which comprise at least one acid function can be chosen from metal salts, for example aluminum ($Al^{3+}$), zinc ($Zn^{2+}$), manganese ($Mn^{2+}$) or copper ($Cu^{2+}$); alkali metal salts, for example lithium ($Li^+$), sodium ($Na^+$) or potassium ($K^+$); or alkaline-earth metal salts, for example calcium ($Ca^{2+}$) or magnesium ($Mg^{2+}$). They can also be ammonium derivatives of formula $NH_4^+$ or organic salts such as ammoniums of formula $Y_3NH^+$, $NY_3$ denoting an organic amine, the Y radicals being identical or different, it being possible for two or three Y radicals to form, in pairs, a ring with the nitrogen atom which carries them or it being possible for $NY_3$ to denote an aromatic amine. The organic amines are for example alkylamines, for instance methylamine, dimethylamine, trimethylamine, triethylamine or ethylamine, or hydroxyalkylamines, for instance 2-hydroxyethylamine, bis(2-hydroxyethyl)amine or tri-(2-hydroxyethyl)amine, or cycloalkylamines, for instance bicyclohexylamine or glucamine, piperidine, or pyridines and the like, for example collidine, quinine or quinoline, or amino acids which are basic in nature, for instance lysine or arginine.

The salts of the compounds of formula (I) which comprise at least one amine function can also be salified with an organic acid such as citric acid, lactic acid, tartaric acid, aspartic acid, glutamic acid, acetic acid, formic acid, trifluoroacetic acid, hydrochloric acid, glycolic acid or malic acid.

In the case where the compounds according to the invention are in salt form, the cations are of course in an amount which ensures the electro-neutrality of the compounds of formula (I).

The mineral salts of the compounds of formula (I) according to the invention can advantageously be chosen from the metal salts $Cu^{2+}$, $Mn^{2+}$ and $Zn^{2+}$, the alkali metal salts $Li^+$, $Na^+$ and $K^+$ and the alkaline-earth metal salts $Ca^{2+}$ and $Mg^{2+}$.

According to another variant, the organic salts of the compounds of formula (I) according to the invention can advantageously be chosen from ammoniums, preferably from the salts of amino acids which are basic in nature, for instance lysine or arginine or from diethanolamine salts or triethanolamine salts.

Preferably, the compounds (I) are in the form of sodium salts $Na^+$.

Preferably, the compounds (I) are in the form of potassium salts $K^+$.

Preferably, the compounds (I) are in the form of calcium salts $Ca^{2+}$.

Another subject of the invention is the novel compounds of formula (I) for which:

S* represents a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;

said radical S* comprising one or more radicals —$OR_s$ and optionally one or two radicals —$NHR'_s$, said monosaccharide or disaccharide radical being connected to the rest of the molecule by a bond between the $C^1$ carbon atom of the sugar or one of the sugars and this bond possibly being α or β anomeric;

X represents an oxygen or sulfur, preferably oxygen, atom;

R' represents:
i) a hydrogen atom;
ii) a ($C_1$-$C_{18}$)alkyl group, preferably ($C_1$-$C_6$)alkyl group such as methyl;
iii) a ($C_1$-$C_{18}$)alkenyl radical, preferably ($C_1$-$C_6$)alkenyl radical, such as prenyl;

iv) an aryl($C_1$-$C_4$)alkyl radical optionally substituted in particular with at least one hydroxyl and/or saturated or unsaturated ($C_1$-$C_4$)alkoxy group, in particular an aryl ($C_1$-$C_4$)alkyl radical such as benzyl;

v) or a ($C_1$-$C_{18}$)alkylcarbonyl, preferably ($C_1$-$C_6$)alkylcarbonyl radical, in particular acetyl ($CH_3$—CO—);

R represents a group chosen from:

i) hydroxyl;

ii) saturated or unsaturated ($C_1$-$C_{18}$)alkoxy, which is preferably saturated and more preferentially saturated $C_1$-$C_6$, such as methoxy, ethoxy, isopropyloxy or tert-butyloxy;

iii) optionally substituted aryl($C_1$-$C_6$)alkoxy, such as benzyloxy;

iv) amino $NR_1R_2$ with $R_1$ and $R_2$ independently denoting a hydrogen atom, a ($C_1$-$C_{16}$)alkyl radical such as methyl, n-propyl, n-hexyl or n-tetradecyl, a ($C_2$-$C_{16}$) alkenyl radical, an aryl radical such as phenyl, or an aryl($C_1$-$C_4$)alkyl group which is optionally substituted in particular with at least one hydroxyl and/or saturated or unsaturated ($C_1$-$C_4$)alkoxy group, such as benzyl;

$R_s$ represents a hydrogen atom or a radical chosen from the radicals: a) methoxymethyl; b) (phenyldimethylsilyl)methoxyphenyl; c) benzyloxymethyl; d) p-methoxybenzyloxymethyl; e) (4-methoxyphenoxy) methyl; f) t-butoxymethyl; g) tetrahydropyranyl; h) tetrahydrofuranyl; i) 2-trimethylsilylethyl; j) t-butyl; k) p-methoxyphenyl; l) p-methoxybenzyl; m) trimethylsilyl; n) triethylsilyl; o) dimethylisopropylsilyl; p) t-butyldimethylsilyl; q) acetyl; r) trifluoroacetyl; s) adamantyl; t) benzoyl; and u) FMOC, said radicals $R_s$ preferably all being identical and all preferably denoting a hydrogen atom or an acetyl radical; and $R'_s$ represents a radical chosen from a hydrogen atom or an acetyl radical, it being understood that:

when S* represents a glucose and R' represents a hydrogen atom, then R is other than a —O-$^t$Bu group; and when S* represents a mannose and R' represents a hydrogen atom, then R is other than a diethylamino group $N(Et)_2$.

Preferably, the novel compounds of formula (I) are such that:

S* denotes a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;

said radical S* comprising one or more radicals —$OR_s$ and optionally one or two radicals —$NHR'_s$, said monosaccharide or disaccharide radical being connected to the rest of the molecule by a bond between the $C^1$ carbon atom of the sugar or one of the sugars and this bond possibly being α or β anomeric;

X denotes an oxygen atom;

R' denotes i) a hydrogen atom;

ii) a ($C_1$-$C_{18}$)alkyl group, preferably ($C_1$-$C_6$)alkyl group such as methyl;

iii) a ($C_1$-$C_{18}$)alkenyl radical, preferably ($C_1$-$C_6$)alkenyl radical, such as prenyl;

iv) an optionally substituted aryl($C_1$-$C_4$)alkyl radical, in particular an aryl($C_1$-$C_4$)alkyl radical such as benzyl;

v) or a ($C_1$-$C_{18}$)alkylcarbonyl, preferably ($C_1$-$C_6$)alkylcarbonyl radical, in particular acetyl ($CH_3$—CO—);

R denotes a group chosen from:

i) hydroxyl;

ii) saturated or unsaturated ($C_1$-$C_{18}$)alkoxy, which is preferably saturated and more preferentially saturated $C_1$-$C_6$, such as methoxy, ethoxy, isopropyloxy or tert-butyloxy;

iii) aryl($C_1$-$C_6$)alkoxy optionally substituted in particular with at least one hydroxyl and/or saturated or unsaturated ($C_1$-$C_4$)alkoxy group such as benzyloxy;

iv) amino $NR_1R_2$ with $R_1$ and $R_2$ independently denoting a hydrogen atom, a ($C_1$-$C_{16}$)alkyl radical such as methyl, n-propyl, n-hexyl or n-tetradecyl, a ($C_2$-$C_{16}$) alkenyl radical, an aryl radical such as phenyl, or an aryl($C_1$-$C_4$)alkyl group which is optionally substituted in particular with at least one hydroxyl and/or saturated or unsaturated ($C_1$-$C_4$)alkoxy group such as benzyl;

$R_s$ denotes a hydrogen atom or an acetyl radical, said radicals $R_s$ all being identical;

$R'_s$ denotes a radical chosen from a hydrogen atom or an acetyl radical.

Advantageously, the novel compound(s) of formula (I) is (are) chosen from the compounds of formula (I'''):

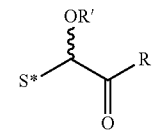

(I''')

and also the solvates thereof such as hydrates, the optical and geometric isomers and tautomers thereof and the organic or mineral base or acid salts thereof, in which formula (I'''), S* and R are as defined above for the novel compounds (I), it being understood that they do not comprise a protective group (PG), and R' denotes a hydrogen atom, acetyl, ($C_1$-$C_{18}$)alkyl, ($C_2$-$C_{18}$)alkenyl or an aryl($C_1$-$C_4$)alkyl radical which is optionally substituted in particular with at least one hydroxyl and/or saturated or unsaturated ($C_1$-$C_4$)alkoxy group, in particular an aryl($C_1$-$C_4$)alkyl radical such as benzyl.

As novel compounds (I), mention may be made of the compounds 1 to 54 defined above.

Preferably, the novel compounds are the novel compounds (I) for which R=—NR1R2 as defined above.

Preferably, S* denotes a sugar chosen from glucose, xylose, rhamnose, mannose, galactose and lactose. More particularly, S denotes a sugar chosen from D-glucose, D-xylose, L-rhamnose, D-mannose, D-galactose and D-lactose.

Preferably, $R_1$ represents a hydrogen atom; and $R_2$ represents a benzyl radical or a linear or branched, saturated or unsaturated $C_1$-$C_{18}$, preferably $C_1$-$C_{16}$, alkyl radical such as methyl, n-propyl, n-hexyl or n-tetradecyl.

More preferentially, $R_1$ represents a hydrogen atom; and $R_2$ represents a linear or branched $C_1$-$C_5$ alkyl radical such as methyl, ethyl, n-propyl, n-butyl or n-pentyl.

In particular, S* denotes a sugar chosen from glucose, xylose, rhamnose, mannose, galactose and lactose; $R_1$ represents a hydrogen atom; and $R_2$ denotes a linear or branched $C_1$-$C_{18}$ alkyl radical; more particularly, $R_2$ denotes a linear or branched $C_1$-$C_{16}$ alkyl radical; preferentially, $R_2$ denotes a radical chosen from methyl, n-propyl, n-hexyl and n-tetradecyl.

More particularly, S* denotes a sugar chosen from glucose, xylose, rhamnose, mannose, galactose and lactose; $R_1$ represents a hydrogen atom; and $R_2$ represents a linear or branched $C_1$-$C_5$ alkyl radical such as methyl, ethyl, n-propyl, n-butyl or n-pentyl.

Preferentially, S* denotes a sugar chosen from glucose; $R_1$ represents a hydrogen atom; and $R_2$ denotes a linear or branched $C_1$-$C_{18}$ alkyl radical; more particularly, $R_2$ denotes a linear or branched $C_1$-$C_{16}$ alkyl radical; preferentially, $R_2$ denotes a radical chosen from methyl, n-propyl, n-hexyl and tetradecyl.

More preferentially, S* denotes a sugar chosen from glucose; $R_1$ represents a hydrogen atom; and $R_2$ represents a linear or branched $C_1$-$C_5$ alkyl radical such as methyl, ethyl, n-propyl, n-butyl or n-pentyl.

For the novel compounds (I) described above, $R_2$ preferably represents a methyl or propyl radical and preferentially a methyl radical.

The preferred novel compounds are the compounds 1 to 24 previously described. The novel compounds that are more preferred are the compounds 1, 2, 5, 6, 9, 10, 13, 14, 17, 18, 21 and 22 described above.

Process for preparing the compounds of formulae (I) et (I''') of the invention

Another subject of the invention is the process for preparing, or a process for the chemical synthesis of, the compounds of formula (I) or (I''') as defined above, according to scheme (1) below:

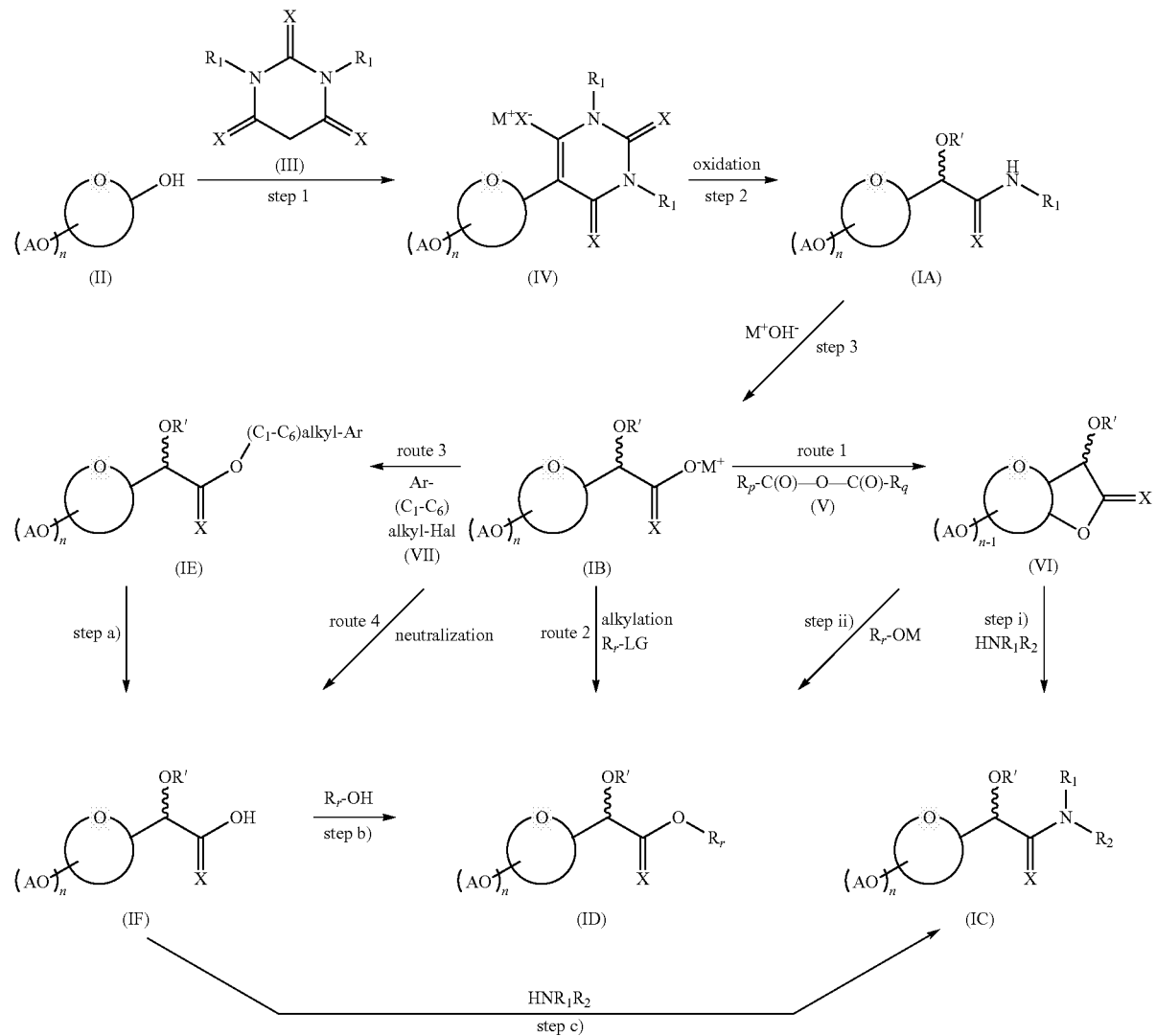

which preparation process comprises the following steps:
step 1 which consists in reacting a monosaccharide or a polysaccharide of formula (II) with a barbituric acid derivative (III), in particular in the presence of a mineral base such as WM⁺OH⁻, M⁺ representing a cationic counterion or preferably a weak base such as (bi)carbonate, in particular with alkali metal (bi)carbonate, or in the presence of an organic base such as triethylamine or diisopropylethylamine,

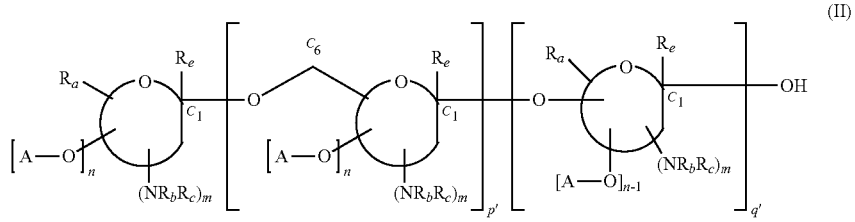

(II)

in which formula (II) A, $R_a$, $R_b$, $R_c$, $R_e$, n, and m are as defined above, p' and q' representing an integer inclusively between 0 and 4, with p'+q' inclusively between 0 and 4, in particular between 0 and 2, preferably p'+q'=0 or 1, it being understood that the two units between square brackets can be reversed; the compound of formula (II) being represented in the scheme by:

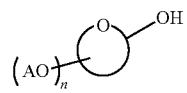

step 1 which is carried out in particular in a polar protic solvent such as water, by heating optionally at a temperature between 30° C. and 100° C., in particular at 80° C., preferably for a period of between 1 hour and 24 hours, in particular between 3 hours and 10 hours, such as 5 hours, so as to give the compound comprising a sugar unit (IV);

step 2 which subsequently consists in reacting the compound (IV) with a chemical oxidizing agent such as hydrogen peroxide or a hydrogen peroxide-generating agent such as oxone, in particular in a polar solvent with a boiling point of between 40° C. and 100° C. at atmospheric pressure, such as acetone or acetonitrile, or a polar protic solvent such as water, optionally in a basic medium and/or in the presence of a chelating agent such as ethylenediaminetetraacetic acid (EDTA) optionally in salt form, so as to give an amide C-glycoside compound (IA) according to the invention, 1) if R' represents a hydrogen atom and it is desired for it to represent a $(C_1-C_{18})$alkyl, $(C_2-C_{18})$alkenyl or $(C_2-C_{18})$alkynyl group, or for the OH group to be protected, then an alkylation step or a step of protecting the hydroxyl function is carried out, if on the other hand R' represents PG, then it can be deprotected if it is desired to obtain a free hydroxyl function, 2) if A represents a hydrogen atom and it is desired to have a PG, then a protection step is added, 3) if $R_b$ and $R_c$ of $NR_bR_c$ represent hydrogen atoms and it is desired to protect the amino group(s), a protection step is carried out, step 3 which subsequently consists in reacting the amide compound (IA) with a base OH⁻M⁺ as defined above so as to give a C-glycoside carboxylate compound (IB) according to the invention; said compound (IB) can then follow 3 synthesis routes:

route 1 which consists in reacting an anhydride (V) of formula $R^p$—C(O)—O—C(O)—$R^q$ with $R^p$ and $R^q$, which may be identical or different, representing a $(C_1-C_4)$alkyl group such as methyl, the anhydride being in particular acetic anhydride, with the compound (IB) so as to give by intramolecular reaction between the oxygen atom of the group A-O at $C^2$ of the first sugar unit directly connected to the rest of the molecule on the C=X after elimination of water so as to give the compound (VI) (more specifically the compounds (VIa), (VIb) and (VIc) as defined below), this compound possibly subsequently either reacting according to step i) with an amine $R_1R_2NH$ so as to give the amide C-glycoside (IC) according to the invention;

or reacting according to step ii) with an alkoxide $R_r$—O⁻M⁺ with $R_r$ representing a $(C_1-C_{18})$alkyl, $(C_2-C_{18})$alkenyl or $(C_2-C_{18})$alkynyl group, and M⁺ representing a cationic counterion, in particular alkali metal or alkaline-earth metal, such as MgBr, Li, Na or K, in a solvent, which is preferably an anhydrous polar solvent, so as to give the ester C-glycoside (ID) according to the invention;

route 2 which consists in reacting the compound (IB) with an alkylating agent comprising a leaving group LG such as mesylate, triflate, tosylate or a halogen such as Cl, Br or I, so as to give the ester C-glycoside (ID) according to the invention;

route 3 which consists in reacting the compound (IB) with an arylalkyl halide (VII): Ar$(C_1-C_6)$alkyl-Hal with Ar representing an aryl and Hal as defined above, preferably (VII) represents a benzyl halide such as benzyl bromide, so as to give the ester C-glycoside (IE) according to the invention; this compound possibly subsequently reacting according to step a) by dealkylarylation (debenzylation) such as by catalytic reduction, for instance hydrogenation with palladium-on-graphite so as to give the acid C-glycoside (IF); this compound possibly subsequently either reacting according to step b) by esterification with an alcohol R$_f$OH, so as to give the ester C-glycoside (IG);

or reacting according to step c) with an amine R$_1$R$_2$NH so as to give the amide C-glycoside (IC) according to the invention;

route 4 which consists in neutralizing (IB) with an organic or mineral acid, so as to give the acid C-glycoside (IF) according to the invention;

it is understood that, depending on the desires for substituents on the radicals R', A and NR$_b$R$_c$, options 1) to 3) mentioned in step 2 also apply to routes 1, 2 and 3 and to steps i), ii), a), b) and c); preferably, the same LG is used for the entire molecule, the compounds (IA) to (IC) being contained in formula (I) according to the invention.

It is also understood that, during the preparation of the reagent (II), steps 2) and 3) mentioned above can be applied thereto.

All the reagents are obtained by conventional methods known by those skilled in the art. The latter will take care to protect or deprotect according to the synthesis steps. For example:

The compounds can be obtained from:

a sugar (II) of scheme 1 comprising OH group(s) which are free or substituted with a C$_1$-C$_6$ alkyl group or with a C$_1$-C$_6$ alkylcarbonyl group, or comprising an OH group protected by a PG that is accessible according to the methods described by Peter G. M. Wuts and Theodora W. Greene, in Greene's Protective Groups in Organic Synthesis, Fourth Edition, Wiley, 2006; processes for alkylation, acylation or protection of the hydroxyls of sugars are known and in particular described in Durantie, Estelle et al, Chemistry—A European Journal, 18(26), 8208-8215 (2012).

The sugar (II) of scheme 1 can also contain one or more amino group(s) substituted with the same C$_1$-C$_6$ alkylcarbonyl group, or with a PG such as those described by Peter G. M. Wuts and Theodora W. Greene, in *Greene's Protective Groups in Organic Synthesis*, Fourth Edition, Wiley, 2006. The processes for alkylation, acylation or protection of the hydroxyls of sugars are known by those skilled in the art and are in particular described in: Durantie, Estelle et al, *Chemistry—A European Journal,* 18(26), 8208-8215 (2012). The N-acylation methods are also well known by those skilled in the art and consist in reacting the amine with either a reactive derivative of a carboxylic acid, such as an acid anhydride or an acid halide (acid chloride), or a carboxylic acid activated in situ via a coupling agent such as HOBt, EDCI, CDI, DCC, HATU or PyBOP, in the optional presence of an organic base such as DI EA or TEA, or of a mineral base such as NaOH, and optionally of DMAP in an equimolar or catalytic amount, in a non-protic polar solvent such as DCM, THF, DMF or ACN, or optionally a protic solvent such as water.

The barbituric acid derivative (III) optionally N-disubstituted with the radicals R$_1$ corresponding to the (C$_1$-C$_{18}$) alkyl, aryl or aryl(C$_1$-C$_4$)alkyl groups, the aryl radical being optionally substituted in particular with OMe, OEt, and/or hydroxyl protected with a PG as defined above; (III) possibly being prepared for example according to the method described by Guoyao Xia et al., *J. Med. Chem.* 2011, 54, 2409-2421.

The hydroxyl group of (IA) in the alpha position with respect to the C═X group (preferably X: oxygen) can be alkylated or acylated so as to give the compound (IA') in which R' is other than H, and corresponds to the groups (C$_1$-C$_{18}$)alkyl, (C$_2$-C$_{18}$)alkenyl, (C$_1$-C$_{18}$)alkynyl, aryl(C$_1$-C$_4$)alkyl, the aryl radical being optionally substituted with a (C$_1$-C$_4$)alkoxy group such as OMe, OEt, and/or hydroxyl optionally protected with a PG (preferably identical to that optionally present on the aryl radical of the group R$_1$), or (C$_1$-C$_{18}$)alkylcarbonyl, or (C$_1$-C$_{18}$)alkenylcarbonyl. R' can also correspond to a protective group for hydroxyl, which may be required in the context of subsequent steps. The step of alkylation of the hydroxyl group is generally carried out by treatment with a base, often a relatively strong base, of NaH, tBuOK or tBuONa type, in the presence of an alkylation agent such as an alkyl halide, in a non-protic polar solvent such as DMF, NMP, THF, ACN or acetone. The step for acylation of the hydroxyl group is generally carried out by treatment with either a reactive derivative of a carboxylic acid, such as an acid anhydride or an acid halide (acid chloride), or a carboxylic acid activated in situ via a coupling agent such as HOBt, EDCI, CDI or DCC, optionally in the presence of a base such as pyridine, triethylamine or diisopropylethylamine, sodium acetate or sodium hydroxide, and optionally of DMAP in an equimolar or catalytic amount, in a non-protic polar solvent such as ACN, pyridine, DCM, THF or acetone, or optionally a protic solvent such as water. Alternatively, the hydroxyl can be treated with a carboxylic acid in an acid medium (APTS, anhydrous HCl, H$_2$SO$_4$), with a device for eliminating the water formed, such as the presence of a desiccant, for instance silica gel, Na$_2$SO$_4$, MgSO$_4$ or P$_2$O$_5$, or a Dean Stark apparatus using a volatile solvent which forms an azeotrope with water, for instance toluene or cyclohexane.

If the hydroxyls of the sugar unit (II) and the hydroxyl in the alpha position with respect to C═X are substituted with the same group, then the starting point is directly the reagent (III) comprising a non-protected sugar unit, in order to subsequently carry out the step of acylation or alkylation of all the hydroxyls in one go on the compound (IA).

It is understood that, when it is necessary to protect the hydroxyl and/or amino functions which might react and parasitize the subsequent reaction, said functions are protected according to the methods known by those skilled in the art previously mentioned, then the reaction in question is carried out, then the hydroxyl and/or amine groups are deprotected by the methods known by those skilled in the art, previously mentioned, so as to again render the hydroxyls and/or amines free.

For example, the following reactions can be carried out by protecting, then carrying out the desired reaction, then deprotecting:

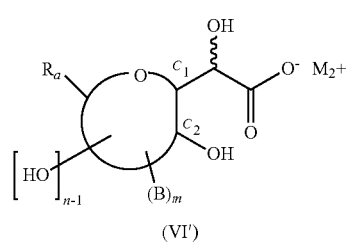
(VI')
Ac₂O →
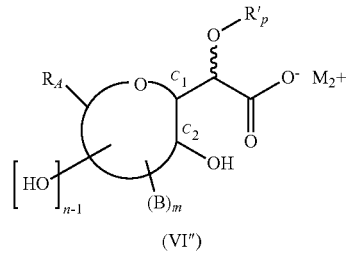
(VII')
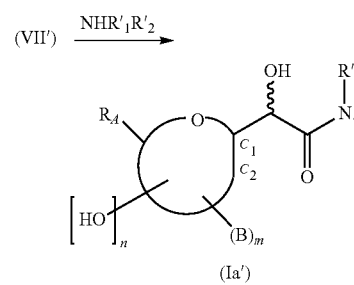
(VI'')
Ac₂O →
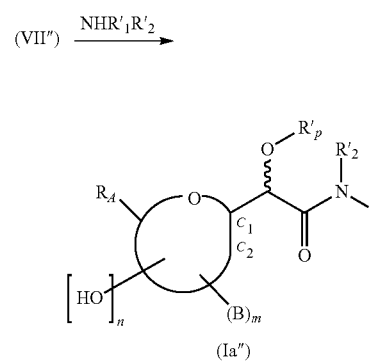
(VII'')
(VII') $\xrightarrow{NHR'_1R'_2}$
(Ia')
(VII'') $\xrightarrow{NHR'_1R'_2}$
(Ia'')
(VII') $\xrightarrow{R''_pO^-}$
-continued
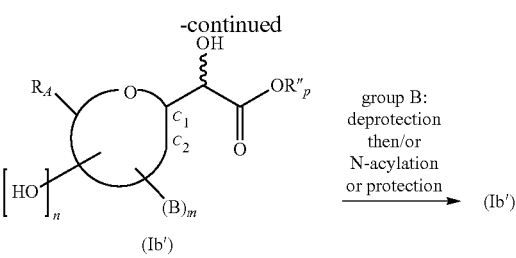
(Ib')
(VII') $\xrightarrow{R''_pO^-}$
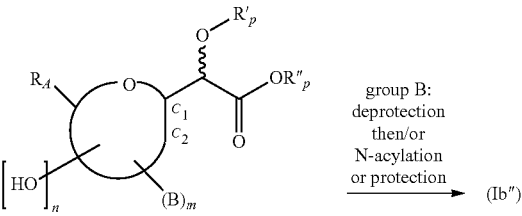
(Ib'')
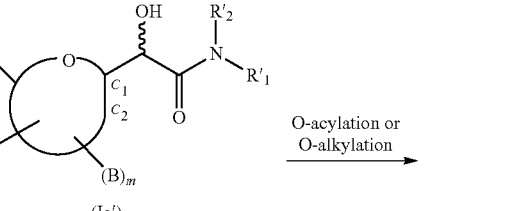
(Ia')
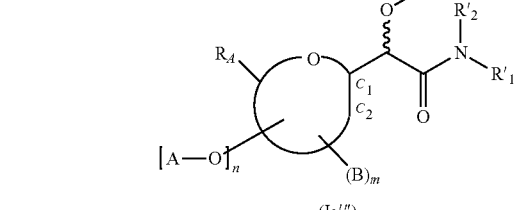
(Ia''')
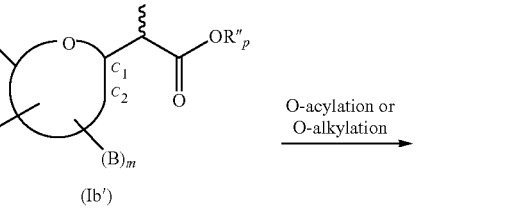
(Ib')
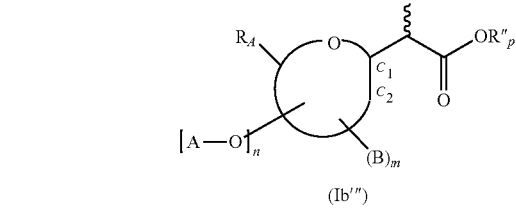
(Ib''')
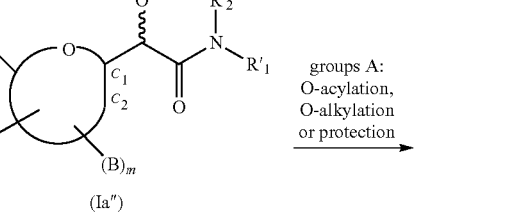
(Ia'')

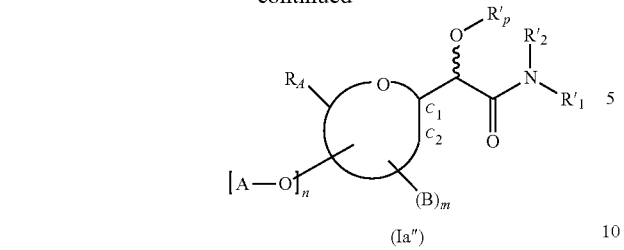

(Ia'')

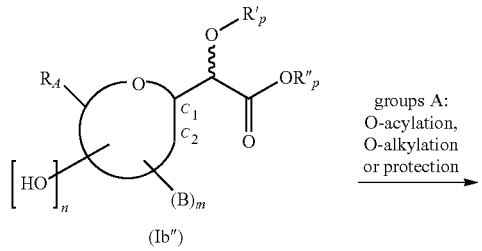

(Ib'')

groups A:
O-acylation,
O-alkylation
or protection
⟶

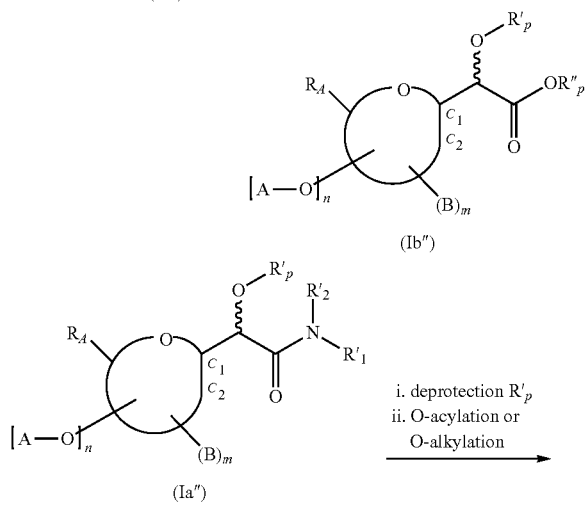

(Ib'')

(Ia'')

i. deprotection R'$_p$
ii. O-acylation or
O-alkylation
⟶

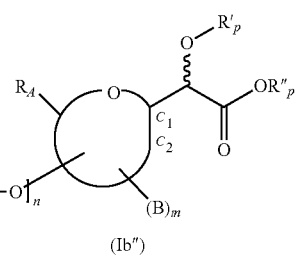

(Ia'')

(Ib'')

i. deprotection R'$_p$
ii. O-acylation or
O-alkylation
⟶

(Ib'')

in which schemes, R'p, R''p represent a protective group or (PG); B and B' denote an amino radical NR$_b$R$_c$ as defined above; R'$_1$, respectively R'$_2$, denotes an R$_1$, respectively R$_2$, group substituted with a protective group, R$_1$ and R$_2$ having the same definitions given above.

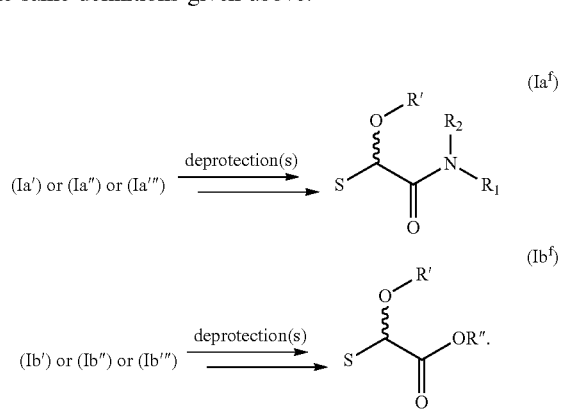

(Ia') or (Ia'') or (Ia''') $\xrightarrow{\text{deprotection(s)}}$ (Ia$^f$)

(Ib') or (Ib'') or (Ib''') $\xrightarrow{\text{deprotection(s)}}$ (Ib$^f$)

Another subject of the invention is the compound (VI) of scheme (1) corresponding to formulae (VIa), (VIb) and (VIc) below:

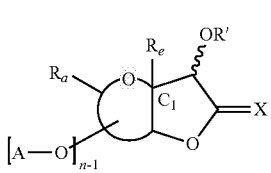

(VIa)

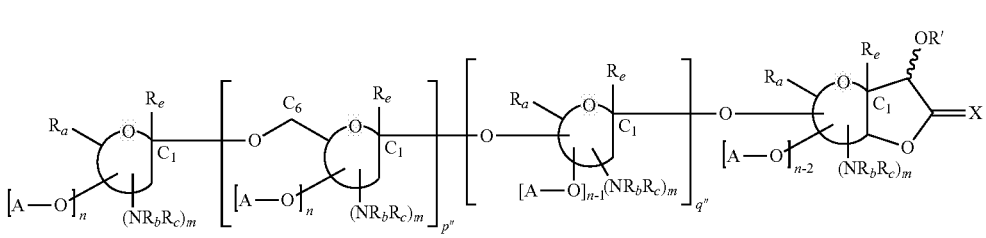

(VIb)

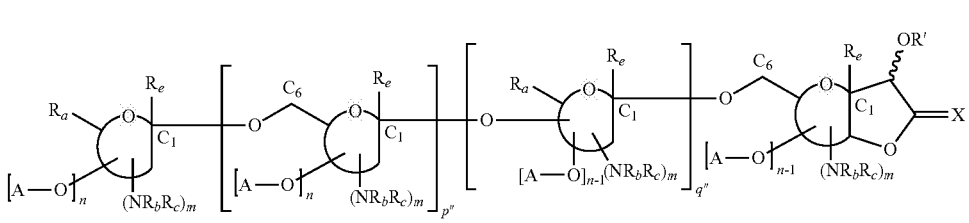

(VIc)

in which formulae (VIa), (VIb) and (VIc):

R', $R_a$, $R_b$, $R_c$, $R_e$, A, X, m, and n are as defined above; in particular —NRbRc represents an —NH-acyl group, and/or A represents in particular a hydrogen atom or an acyl group, preferably an acyl group;

p" and q" are integers inclusively between 0 and 3, with p"+q" between 0 and 3, particularly between 0 and 1; such as 0;

it being understood that, for (VIb) and (VIc), the two sugar units between square brackets with the indices p" and q" may be reversed.

As compounds of formula (I), use may be made of the compounds 1 to 54 previously described. As compounds of formula (V), use may be made of the compounds 1 to 54 in which all the hydroxyl groups of the sugar are substituted with a group chosen from acetyl, THP, TMS, TBDMS, tosyl, tert-butyl, MOM and benzoate, and in particular the compounds 1 to 54 in which all the hydroxyl groups of the sugar are substituted with an identical group chosen from the list above, said group preferentially denoting acetyl.

The present invention also relates to a composition comprising, in a physiologically acceptable medium, a compound of formula (I') or (I''') as described above. The composition is in particular a cosmetic composition.

According to one advantageous form of the invention, the cosmetic composition contains at least one compound of formula (I) or (I''') as defined above and at least one additive chosen from a fragrance, a thickener, a surfactant, a pigment, a dye and a preservative.

More particularly, the cosmetic composition according to the invention contains at least one compound chosen from the compounds 1 to 54 defined above, and also the solvates thereof such as hydrates, and the organic or mineral acid or base salts thereof.

The compound of formula (I''') or (I) (each compound of formula (I) or (I''') if the composition comprises several thereof) may be present in the composition in an amount which may be between 0.01 and 10% by weight, preferably between 0.1 and 5% by weight, in particular between 0.5 and 3% by weight, relative to the total weight of the composition.

A subject of the invention is also a process for cosmetic treatment of the skin, comprising the application to the skin of a composition comprising at least one compound of formula (I) or (I''') as defined above.

In particular, the treatment process aims to prevent the signs of skin aging. Preferably, the treatment process aims to treat the signs of skin aging.

It also relates to a process for cosmetic treatment of the skin intended to prevent and/or treat aging, comprising at least one step which consists in applying to skin exhibiting signs of skin aging at least one composition comprising a compound of formula (I) or (I''') as defined above.

In particular, the process according to the invention aims to improve the radiance and/or the uniformity of the complexion; to improve the radiance and/or the transparency of the skin; to improve the softness, the suppleness and/or the elasticity of the skin; and/or to prevent and/or reduce wrinkles and/or fine lines.

The compounds of formula (I) or (I''') are in particular useful as agents for combating the signs of aging, in particular chronobiological aging, of the skin.

The present invention also relates to the use of at least one compound of formula (I) or (I'''), a salt thereof, or a solvate thereof, for preparing a composition intended for combating the signs of aging, in particular of chronobiological aging, of the skin. It also relates to the use of at least one compound of formula (I) or (I''') as defined above, in a cosmetic composition comprising a physiologically acceptable medium, as an agent intended for combating the signs of skin aging.

The present invention also relates to the use of a compound or of a composition according to the invention for combating the signs of aging, in particular chronobiological aging, of the skin.

The compounds or compositions according to the invention are in particular intended for correcting all skin re-epithelialization disorders.

In this respect, use will in particular be made of the compounds of formula (I) or of formula (I''') such that:

S* represents a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;

said radical S* comprising one or more radicals —$OR_s$ and optionally one or two radicals —$NHR'_s$, said monosaccharide or disaccharide radical being connected to the rest of the molecule by a bond between the $C^1$ carbon atom of the sugar or one of the sugars and this bond possibly being α or β anomeric;

X represents an oxygen atom or a sulfur atom, preferably an oxygen atom;

R' represents:

i) a hydrogen atom;

ii) a ($C_1$-$C_{18}$)alkyl group, preferably ($C_1$-$C_6$)alkyl group such as methyl;

iii) a ($C_1$-$C_{18}$)alkenyl radical, preferably ($C_1$-$C_6$)alkenyl radical, such as prenyl;

iv) an aryl($C_1$-$C_4$)alkyl radical optionally substituted in particular with at least one hydroxyl and/or saturated or unsaturated ($C_1$-$C_4$)alkoxy group, in particular an aryl ($C_1$-$C_4$)alkyl radical such as benzyl;

v) or a ($C_1$-$C_{18}$)alkylcarbonyl, or preferably ($C_1$-$C_6$)alkylcarbonyl radical, in particular acetyl ($CH_3$—CO—);

R represents a group chosen from:

i) hydroxyl;

ii) saturated or unsaturated ($C_1$-$C_{18}$)alkoxy, which is preferably saturated and more preferentially saturated $C_1$-$C_6$, such as methoxy, ethoxy, isopropyloxy or tert-butyloxy;

iii) optionally substituted aryl($C_1$-$C_6$)alkoxy, such as benzyloxy;

iv) amino $NR_1R_2$ with $R_1$ and $R_2$ independently denoting a hydrogen atom, a ($C_1$-$C_{16}$)alkyl radical such as methyl, n-propyl, n-hexyl or n-tetradecyl, a ($C_2$-$C_{16}$) alkenyl radical, or an aryl($C_1$-$C_4$)alkyl group which is optionally substituted in particular with at least one hydroxyl and/or saturated or unsaturated ($C_1$-$C_4$) alkoxy group, such as benzyl;

$R_s$ represents a hydrogen atom or a radical chosen from the radicals: a) methoxymethyl; b) (phenyldimethylsilyl)methoxyphenyl; c) benzyloxymethyl; d) p-methoxybenzyloxymethyl; e) (4-methoxyphenoxy)methyl; f) t-butoxymethyl; g) tetrahydropyranyl; h) tetrahydrofuranyl; i) 2-trimethylsilylethyl; j) t-butyl; k) p-methoxyphenyl; l) p-methoxybenzyl; m) trimethylsilyl; n) triethylsilyl; o) dimethylisopropylsilyl; p) t-butyldimethylsilyl; q) acetyl; r) trifluoroacetyl; s) adamantyl; t) benzoyl; and u) FMOC, said radicals $R_s$ preferably all being identical and all preferably denoting a hydrogen atom or an acetyl radical;

$R'_s$ represents a radical chosen from a hydrogen atom or an acetyl radical.

According to another variant, use will be made in particular of a compound of formula (I) or (I''') such that S* denotes a monosaccharide sugar radical chosen from: glucose, galactose, mannose, xylose, lyxose, fucose, arabinose, rhamnose, quinovose, fructose, sorbose, talose, N-acetylglucosamine, N-acetylgalactosamine, glucosamine and galactosamine; or a disaccharide chosen from: lactose, maltulose, palatinose, lactulose, amygdalose, turanose, cellobiose, isomaltose, rutinose and maltose;

said radical S* comprising one or more radicals —$OR_s$ and optionally one or two radicals —$NHR'_s$;

said monosaccharide or disaccharide radical being connected to the rest of the molecule by a bond between the $C^1$ carbon atom of the sugar or one of the sugars and this bond possibly being α or β anomeric;

X denotes an oxygen atom;

R' denotes
  i) a hydrogen atom;
  ii) a ($C_1$-$C_{18}$)alkyl group, preferably ($C_1$-$C_6$)alkyl group such as methyl;
  iii) a ($C_1$-$C_{18}$)alkenyl radical, preferably ($C_1$-$C_6$)alkenyl radical, such as prenyl;
  iv) an optionally substituted aryl($C_1$-$C_4$)alkyl radical, in particular an aryl($C_1$-$C_4$)alkyl radical such as benzyl;
  v) or a ($C_1$-$C_{18}$)alkylcarbonyl, or preferably ($C_1$-$C_6$)alkylcarbonyl radical, in particular acetyl ($CH_3$—CO—);

R denotes a group chosen from:
  i) hydroxyl;
  ii) saturated or unsaturated ($C_1$-$C_{18}$)alkoxy, which is preferably saturated and more preferentially saturated $C_1$-$C_6$, such as methoxy, ethoxy, isopropyloxy or tert-butyloxy;
  iii) aryl($C_1$-$C_6$)alkoxy optionally substituted in particular with at least one hydroxyl and/or saturated or unsaturated ($C_1$-$C_4$)alkoxy group such as benzyloxy;
  iv) amino $NR_1R_2$ with $R_1$ and $R_2$ independently denoting a hydrogen atom, a ($C_1$-$C_{16}$)alkyl radical such as methyl, n-propyl, n-hexyl or n-tetradecyl, a ($C_2$-$C_{16}$) alkenyl radical, or an aryl($C_1$-$C_4$)alkyl group which is optionally substituted in particular with at least one hydroxyl and/or saturated or unsaturated ($C_1$-$C_4$) alkoxy group, such as benzyl;

$R_s$ denotes a hydrogen atom or an acetyl radical, said radicals $R_s$ all being identical;

$R'_s$ denotes a radical chosen from a hydrogen atom or an acetyl radical.

More particularly, use will be made of a compound chosen from the compounds 1 to 54 defined above, and also the solvates thereof such as hydrates, and the organic or mineral acid or base salts thereof.

The compounds or compositions according to the invention are particularly suitable for combating the signs of chronobiological aging of the epidermis. During chronobiological aging, the thickness of the epidermis becomes reduced, the cell divisions decreasing in number. By facilitating cell multiplication, in particular epidermal cell multiplication, the regeneration of the epidermis is facilitated and the skin has a younger appearance.

The compounds or compositions according to the invention are in particular intended for preventing or reducing wrinkles and fine lines, and/or thinning of the skin and/or the flaccid and/or withered skin appearance. The present invention thus also relates to the use of at least one compound according to the invention in a cosmetic composition for preventing or reducing wrinkles and fine lines, and/or thinning of the skin and/or the flaccid and/or withered skin appearance.

The composition also comprises a physiologically acceptable medium, which is preferentially a cosmetically or pharmaceutically acceptable medium, in particular a dermatologically acceptable medium, i.e. a medium that has no unpleasant odour, color or appearance, and that does not cause the user any unacceptable stinging, tautness or redness. In particular, the composition is suitable for topical application to the skin and skin appendages.

The term "physiologically acceptable medium" is intended to mean a medium that is compatible with human skin and skin appendages.

The composition according to the invention may then comprise any adjuvant commonly used in the envisaged application field.

Mention may be made in particular of water; organic solvents, in particular $C_1$-$C_6$ alcohols and $C_2$-$C_{10}$ carboxylic acid esters; carbon-based and/or silicone oils, of mineral, animal and/or plant origin; water, waxes, pigments, fillers, dyes, surfactants, emulsifiers, coemulsifiers; cosmetic or dermatological active agents, UV-screening agents, polymers, hydrophilic or lipophilic gelling agents, thickeners, preservatives, fragrances, bactericides, odour absorbers and antioxidants.

These optional adjuvants may be present in the composition in a proportion of from 0.001% to 80% by weight and in particular from 0.1% to 40% by weight relative to the total weight of the composition.

The composition according to the invention may constitute a makeup composition, or preferentially a skincare composition, and in particular a cleansing, protecting, treating or care cream for the face, the hands, the feet, the major anatomical folds or the body (for example day creams, night creams, makeup-removing creams, foundation creams or anti-sun creams); a fluid foundation, a makeup-removing milk, a protective or care body milk or an anti-sun milk; a skincare lotion, gel or mousse, such as a cleansing lotion, or a hair composition.

The composition according to the invention is advantageously an anti-aging, in particular care, composition intended for treating and/or combating, cosmetically, the external signs of skin aging; the composition is more particularly a care composition for mature skin.

The invention is illustrated in greater detail by the following non-limiting examples.

EXAMPLES

Example 1: Synthesis of Compound 1

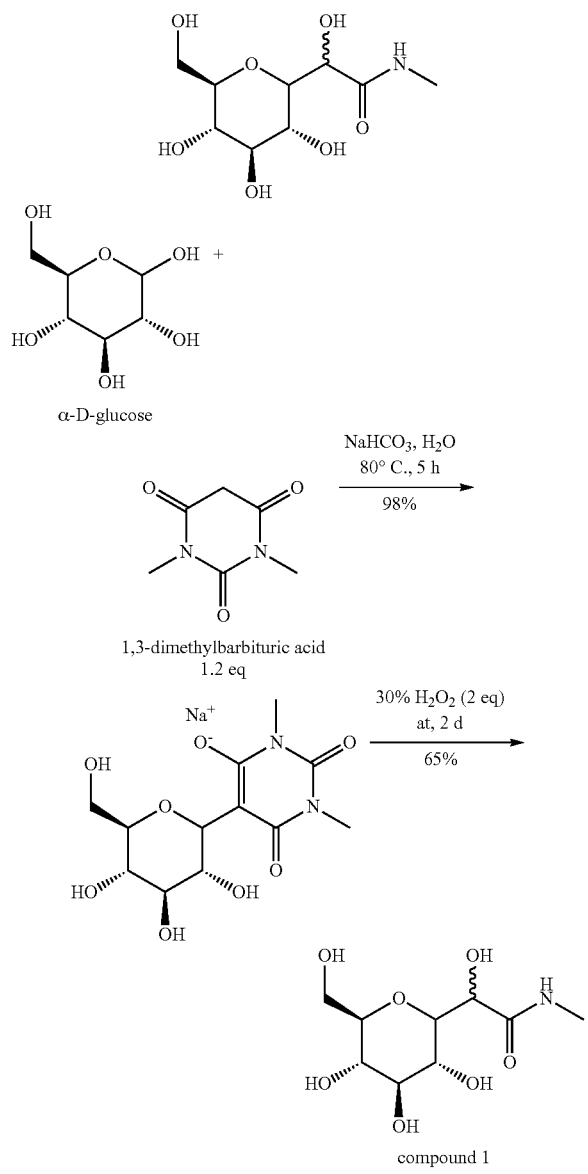 [SMILES: CNC(=O)C(O)C1O[C@H](CO)[C@@H](O)[C@H](O)[C@H]1O ; OC[C@H]1OC(O)[C@H](O)[C@@H](O)[C@@H]1O ; CN1C(=O)CC(=O)N(C)C1=O ; Cn1c([O-])c(C2O[C@H](CO)[C@@H](O)[C@H](O)[C@H]2O)c(=O)n(C)c1=O ; [Na+] ; CNC(=O)C(O)C1O[C@H](CO)[C@@H](O)[C@H](O)[C@H]1O]

Step 1.

D-glucose (5 g), dissolved in water (56 ml), is introduced into a 250 ml single-necked round-bottomed flask. 1,3-Dimethylbarbituric acid (4.33 g) is added with stirring, then $NaHCO_3$ is added up to pH 7. After neutralization, the round-bottomed flask is equipped with a condenser and the mixture is heated at 80° C. for 5 h. The reaction is monitored by TLC in 1:1 DCM/MeOH. The reaction mixture is concentrated under vacuum. The residue obtained is taken up in water, then precipitated from acetone and filtered and the solid obtained is dried under vacuum. Orange powder, 9.3 g, yield 98%. The $^1$H NMR spectra and the mass spectrometry are in accordance with the expected structure.

Step 2.

5 g of the product obtained in step 1 are diluted in 10 ml of water at ambient temperature, then 30% $H_2O_2$ (3 ml) is added. The reaction mixture is stirred at ambient temperature for 2 days. The reaction is monitored by TLC in BuOH/AcOH/$H_2O$ (3/1/1). 0.21 equiv. of an aqueous 20% sodium metabisulfite solution is then added, and stirring is continued for 1 h at ambient temperature. The absence of peroxide is verified, then the reaction mixture is poured into 300 ml of ethanol. The precipitate formed is filtered off, and the filtrate is concentrated to a minimum volume. The second fraction of solid is collected and the two fractions are dried under vacuum at 30° C. (1.6 g). The filtrate is again taken up in ethanol, the precipitate formed is filtered off, and the filtrate is concentrated to dryness to give another product fraction (0.8 g). White solid, 2.4 g, yield 65%. The $^1$H/$^{13}$C NMR spectra and the mass spectrometry are in accordance with the expected structure.

Example 2: Synthesis of Compound 5

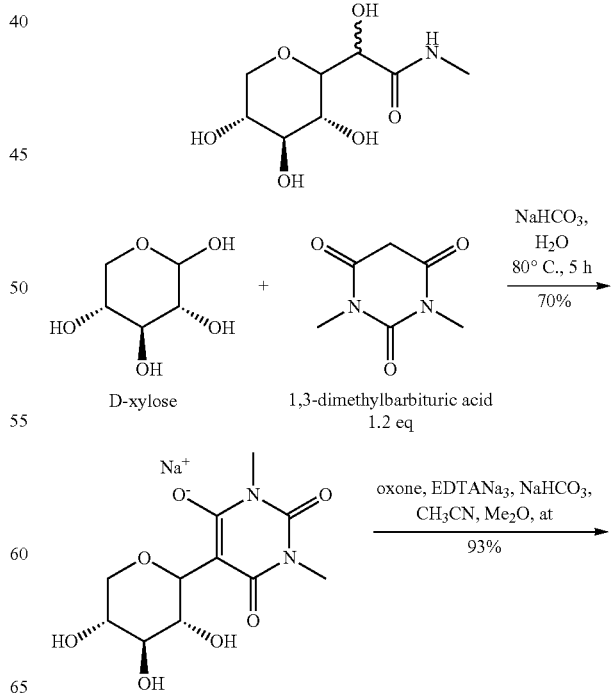

-continued

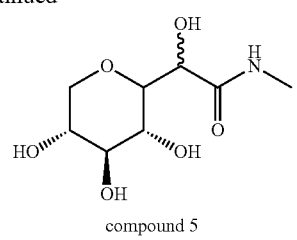

compound 5

Step 1.

According to the process described in example 1, the intermediate is obtained from D-xylose. Yield 70%.

Step 2.

5 g of the product obtained in step 1 are diluted in 80 ml of acetonitrile at a.t. 7 mg (0.0012 eq) of EDTANa$_2$ diluted beforehand in 46 ml of water (C=4·10$^{-4}$ M) are added. The mixture is placed in an ice bath and then 13 ml of acetone are added thereto. The oxone (25.2 g, 2.5 eq)/NaHCO$_3$ (10.5 g, 8 eq) mixture is slowly added to the reaction medium (approximately two spatulas every 10 minutes). The pH variations must be controlled at each addition. The solution becomes white. The mixture obtained is filtered through a Büchner funnel, then the solvent is evaporated off in a rotary evaporator and the product is dried under vacuum. White powder, 3.38 g, yield 93%. The $^1$H/$^{13}$C NMR spectra and the mass spectrometry are in accordance with the expected structure.

Example 3: Synthesis of Compound 9

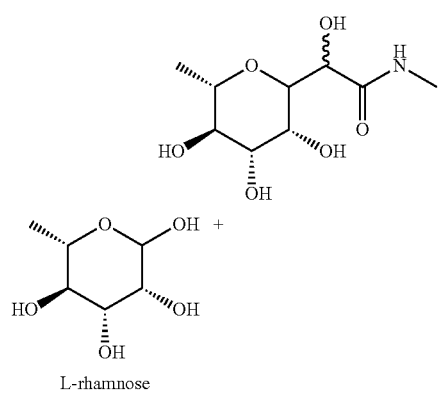

L-rhamnose

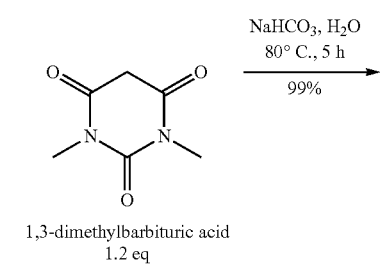

1,3-dimethylbarbituric acid
1.2 eq

NaHCO$_3$, H$_2$O
80° C., 5 h
99%

-continued

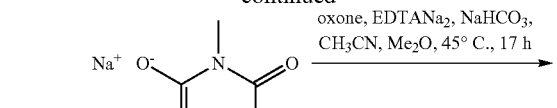

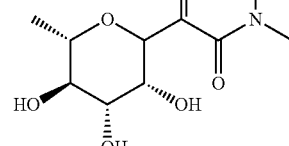

oxone, EDTANa$_2$, NaHCO$_3$,
CH$_3$CN, Me$_2$O, 45° C., 17 h

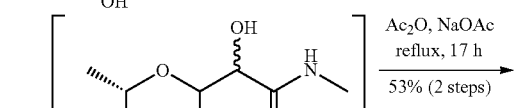

Ac$_2$O, NaOAc
reflux, 17 h
53% (2 steps)

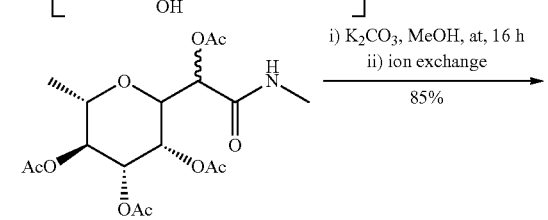

i) K$_2$CO$_3$, MeOH, at, 16 h
ii) ion exchange
85%

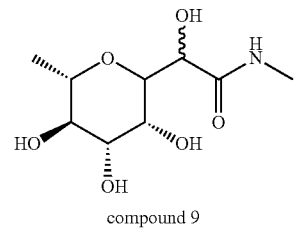

compound 9

Step 1.

According to the process described in example 1, the intermediate is obtained from L-rhamnose (3.4 g, 20.8 mmol). Yield 99%.

Step 2.

According to the process described in example 2, the crude compound 9 is obtained after filtration (5.5 g).

Step 3.

A mixture of the crude compound 9 (5.5 g, 20.8 mmol) and NaOAc.3H$_2$O (4.24 g, 31.2 mmol) in 100 ml of Ac$_2$O (acetic anhydride) is stirred at 100° C. for 16 h. After cooling, the mixture is poured in to 160 ml of a water/ice bath and extracted 3 times with diethyl ether. The organic phases are combined, and washed three times with saturated NaHCO$_3$ and five times with H$_2$O. The solvent is evaporated off under vacuum, and the residue obtained is purified by silica chromatography (20% ethyl acetate in hexane), then recrystallized from ethanol to give 4.74 g of acetylated intermediate in the form of a white solid, yield 53% (2 steps). The $^1$H NMR spectra and the mass spectrometry are in accordance with the expected structure.

Step 4.

A mixture of the product obtained in step 3 (4.74 g, 11 mmol) and K$_2$CO$_3$ (3.04 g, 22 mmol) in 80 ml of methanol is stirred at a.t. for 16 h. The ion exchange resin IR-120 (12 g) washed in absolute methanol is then added. The mixture is then stirred for 30 min, and the resin is removed by filtration. The solvent is evaporated off under vacuum to give 2.2 g of pure compound 9 in the form of a white solid, yield 85%. The $^1$H/$^{13}$C NMR spectra and the mass spectrometry are in accordance with the expected structure.

Example 4: Synthesis of Compound 13

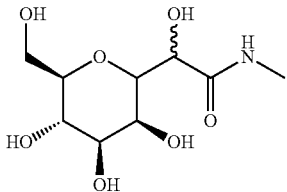 [SMILES: CNC(=O)C(O)C1O[C@H](CO)[C@@H](O)[C@H](O)[C@@H]1O]

According to the process described in example 3, the compound 13 is obtained from D-mannose (5.85 g, 32.5 mmol). White solid, 2.8 g, yield steps 1+2+3=68%, yield step 4=86%. The $^1$H/$^{13}$C NMR spectra and the mass spectrometry are in accordance with the expected structure.

Example 5: Synthesis of Compound 17

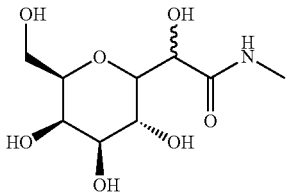 [SMILES: CNC(=O)C(O)C1O[C@H](CO)[C@H](O)[C@H](O)[C@H]1O]

According to the process described in example 3, the compound 17 is obtained from D-galactose (5 g, 27.8 mmol). White solid, 2.4 g, yield steps 1+2+3=53%, yield step 4=83%. The $^1$H/$^{13}$C NMR spectra and the mass spectrometry are in accordance with the expected structure.

Example 6: Synthesis of Compound 21

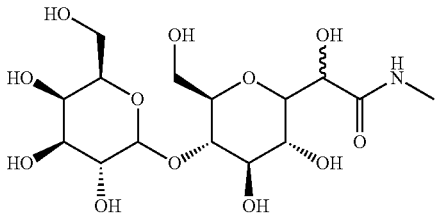 [SMILES: CNC(=O)C(O)C1O[C@H](CO)[C@@H](OC2O[C@H](CO)[C@H](O)[C@H](O)[C@H]2O)[C@H](O)[C@H]1O]

According to the process described in example 3, the compound 21 is obtained from D-lactose (6.2 g, 17 mmol). White solid, 3 g, yield steps 1+2+3=56%, yield step 4=83%. The $^1$H/$^{13}$C NMR spectra and the mass spectrometry are in accordance with the expected structure.

Example 7: Synthesis of Compound 49

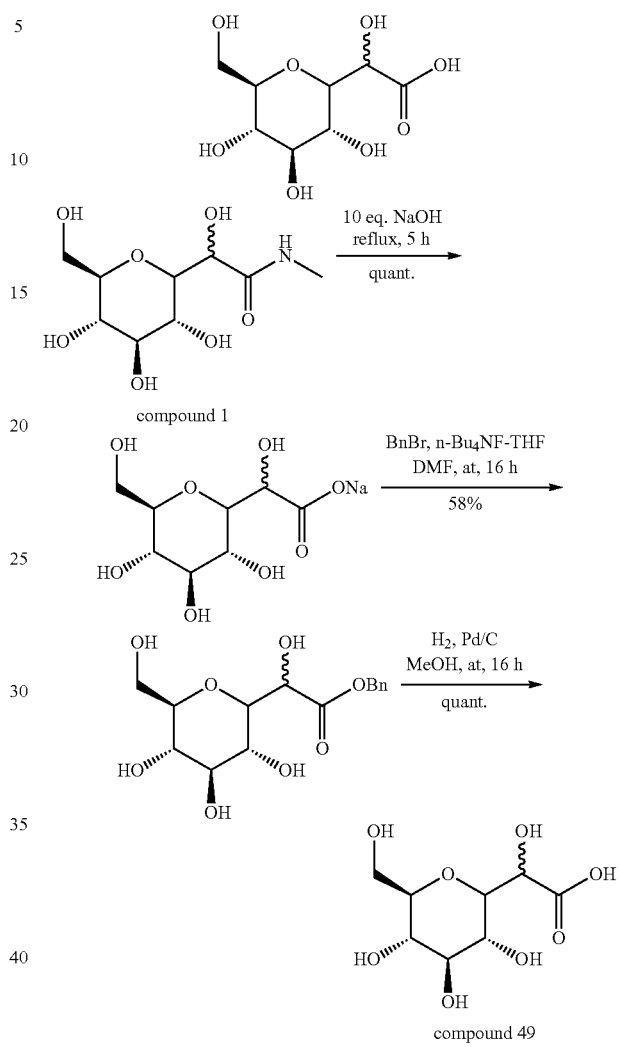

Step 1.

The compound 1 (2.56 g, 10 mmol) is added to a solution of NaOH (4 g, 100 mmol) in 50 ml of water. After stirring at 100° C. for 5 h, the reaction mixture is adjusted to pH~4 by adding an ion exchange resin. The resin is then removed by filtration. The filtrate is concentrated to give 2.3 g of the acid salt in the form of a gray solid, quantitative yield. The $^1$H NMR spectra and the mass spectrometry are in accordance with the expected structure.

Step 2.

A mixture of the salt obtained in step 1 (3.3 g, 12.6 mmol), benzyl bromide (2.6 g, 15.2 mmol), 12.6 ml of n-Bu$_4$NF in 1 M solution in THF, and 20 ml of DMF, is stirred at a.t. for 16 h. The mixture is then concentrated to dryness. The residue is purified by silica column chromatography (dichloromethane/methanol=10/1) to give 2.4 g of the benzyl ester in the form of a white solid, yield 58%. The $^1$H NMR spectra and the mass spectrometry are in accordance with the expected structure.

Step 3.

50 mg of Pd/C are added to a solution of the ester obtained in step 2 (950 mg, 2.9 mmol) in 20 ml of methanol. The mixture is stirred at a.t. under $H_2$ for 16 h. After filtration, the filtrate is concentrated to dryness to give 720 mg of compound 49 in the form of a white solid, quantitative yield. The $^1H/^{13}C$ NMR spectra and the mass spectrometry are in accordance with the expected structure.

Example 8: Synthesis of Compound 2

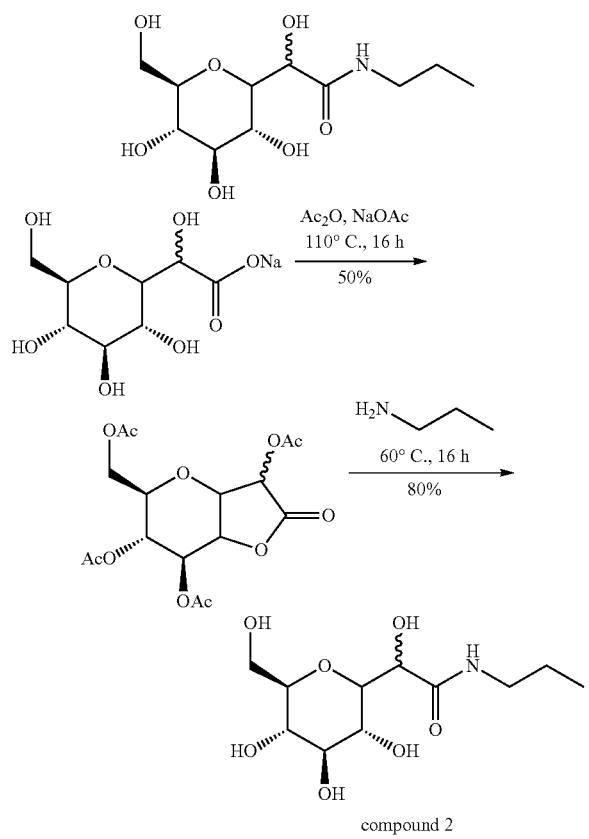

compound 2

Step 1.

A mixture of the acid salt described in example 7 (2.5 g, 10 mmol), NaOAc (2 g, 10 mmol), and 20 ml of $Ac_2O$ is stirred at 110° C. for 16 h. The mixture is then concentrated to dryness. The residue is taken up in 200 ml of sat. aq. $NaHCO_3$ and extracted 3 times with ethyl acetate. The organic phases are combined and concentrated under vacuum, and the residue obtained is purified by silica chromatography (petroleum ether/ethyl acetate=2/1) to give 1.9 g of the lactone intermediate in the form of a white solid, yield 50%. The $^1H$ NMR spectra and the mass spectrometry are in accordance with the expected structure.

Step 2.

A mixture of the lactone obtained in step 1 (1.9 g, 5 mmol) and 10 ml of propylamine is stirred at 60° C. for 16 h. The mixture is then concentrated to dryness. The residue obtained is recrystallized from ethyl acetate to give 1.1 g of compound 2 in the form of a pale yellow solid, yield 80%.

The $^1H/^{13}C$ NMR spectra and the mass spectrometry are in accordance with the expected structure.

Example 9: Synthesis of Compound 3

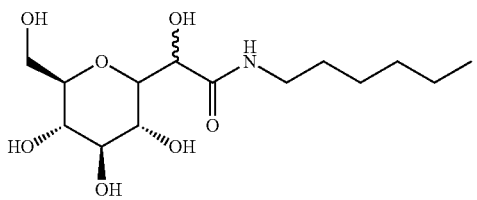 [SMILES: CCCCCCNC(=O)C(O)C1O[C@H](CO)[C@@H](O)[C@H](O)[C@H]1O]

According to the process described in example 8, the compound 3 is obtained from the lactone intermediate (2.5 g, 6 mmol) and 10 ml of n-hexylamine after 16 h at 100° C. Recrystallization from ethyl acetate. Pale yellow solid, 1.6 g, yield 83%. The $^1H/^{13}C$ NMR spectra and the mass spectrometry are in accordance with the expected structure.

Example 10: Synthesis of Compound 4

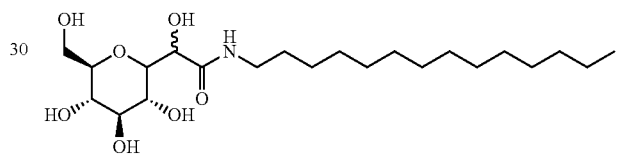

According to the process described in example 8, the compound 4 is obtained from the lactone intermediate (1 g, 2.57 mmol) and n-tetradecylamine (2.8 g, 12.85 mmol), after 6 h at 150° C. Recrystallization from ethyl acetate. Pale yellow solid, 0.9 g, yield 81%. The $^1H/^{13}C$ NMR spectra and the mass spectrometry are in accordance with the expected structure.

Example 11: Biological Activity of the Compounds 1 and 4

Normal human keratinocytes (NHKs) were seeded and cultured in culture medium for 24 hours and then in test medium for a further 24 hours. After incubation, the medium was replaced with test medium containing or not containing (control) the test compounds or the references, and then the cells were incubated for 48 hours. All the experimental conditions were performed in n=3. After incubation, the culture medium was removed and the cells were rinsed, fixed and permeabilized. GLUT-1 expression was determined by immuno labeling.

| GLUT-1 expression vs 100% control | |
|---|---|
| Compound 1 (10 μM) | Reference 2 mM metformine |
| 159% (p < 0.05) | 252% (p < 0.01) |

-continued

| GLUT-1 expression vs 100% control | |
| --- | --- |
| Compound 4 (10 μM) | Reference 2 mM metformine |
| 142% (p < 0.01) | 296% (p < 0.001) |

The expression of the GLUT-1 protein is very significantly stimulated by the compounds 1 and 4.

Example 12

An anti-aging gel for the skin is prepared, comprising (% by weight):

| | |
| --- | --- |
| compound of example 1 | 2% |
| hydroxypropylcellulose (Klucel H from Hercules) | 1% |
| fragrance, preservative | qs |
| isopropanol | 40 |
| water | qs 100% |

A similar composition is prepared with the compound of example 2.

Example 13: Study of the Effects of Compounds (I) on the Synthesis of Total Glycosaminoglycans in Normal Human Epidermal Keratinocytes The study is carried out by measuring the incorporation of radioactive glucosamine into the matrix neosynthesized by cultures of normal human epidermal keratinocytes. The incorporation of radioactive [$^3$H]-glucosamine indicates a specific neosynthesis of total glycosaminoglycans.

The test is carried out on a culture of normal human epidermal keratinocytes in a 96-well plate and cultured in culture medium for 24 hours:

Culture medium: Keratinocytes-SFM supplemented with 0.5 ng/ml epidermal growth factor (EGF), 25 μg/ml pituitary extract, 25 μg/ml gentamycin.

Culture conditions: 37° C.; 5% $CO_2$

The medium was then replaced with culture medium containing or not containing (control) the compound (I) tested or the references 4-nitrophenyl-B-D-xylopyranoside (tested at 300 μM) and 4-methylumbelliferyl-B-D-xylopyranoside (tested at 54 μM) or the solvent control (DMSO at 0.1%), then the cells were incubated for 72 hours with addition of the [$^3$H]-glucosamine label for the final 24 hours of incubation.

The test was carried out with 3 assays for each compound tested, at the concentrations of 1, 10, 100 and 300 μM.

At the end of the incubation, the glycosaminoglycans were extracted from the cells with a chaotropic buffer. The level of radioactive glucosamine incorporated is measured at the end of the test by adsorption of the anionic molecules on Q-sepharose beads, followed by desorption of the molecules having low and medium anionicity with 6M urea plus 0.2 M NaCl. Once washed, the radioactivity incorporated into the very cationic molecules remaining on the support is counted.

The results were evaluated relative to a control constituted of cells which had not been treated with the compound (I).

A positive control (TGFβ at 0.25 ng/ml) known to stimulate GAG synthesis was introduced into the test carried as a positive reference.

The results are given in the following table:

| Treatment | | Mean value | sd | n | % | p |
| --- | --- | --- | --- | --- | --- | --- |
| Control | | 15109 | 892 | 3-3 | 100 | — |
| 4-nitrophenyl β-D-xylopyranoside | | 31280 | 544 | 3 | 207 | <0.001 |
| 4-methylumbelliferyl-β-D-xylopyranoside | | 32202 | 670 | 3 | 213 | <0.001 |
| Solvent control (0.1% DMSO) | | 17863 | 932 | 3-3 | 118 | >0.05 |
| Compound 1 | 1 μM | 21591 | 293 | 3 | 125 | 0.01 < p < 0.05 |
| | 10 μM | 20216 | 709 | 3 | 117 | p > 0.05 |
| | 100 μM | 20451 | 898 | 3 | 118 | p > 0.05 |
| | 300 μM | 16850 | 2070 | 3 | 97 | p > 0.05 |
| Compound 2 | 1 μM | 14638 | 838 | 3 | 110 | p > 0.05 |
| | 10 μM | 16779 | 1032 | 3 | 126 | 0.01 < p < 0.05 |
| | 100 μM | 16435 | 2319 | 3 | 123 | p > 0.05 |
| | 300 μM | 16929 | 1865 | 3 | 127 | p > 0.05 |
| Compound 5 | 1 μM | 17792 | 1030 | 3 | 134 | 0.01 < p < 0.05 |
| | 10 μM | 16133 | 1949 | 3 | 121 | p > 0.05 |
| | 100 μM | 15835 | 2289 | 3 | 119 | p > 0.05 |
| | 300 μM | 15495 | 2171 | 3 | 116 | p > 0.05 |
| Compound 9 | 1 μM | 16162 | 2008 | 3 | 120 | p > 0.05 |
| | 10 μM | 15439 | 985 | 3 | 114 | p > 0.05 |
| | 100 μM | 17655 | 2224 | 3 | 131 | p > 0.05 |
| | 300 μM | 22845 | 400 | 3 | 169 | <0.001 |
| Compound 13 | 1 μM | 16090 | 1523 | 3 | 119 | p > 0.05 |
| | 10 μM | 17340 | 598 | 3 | 129 | 0.001 < p < 0.01 |
| | 100 μM | 18139 | 2075 | 3 | 134 | p > 0.05 |
| | 300 μM | 18804 | 301 | 3 | 139 | p > 0.05 |
| Compound 17 | 1 μM | 17387 | 815 | 3 | 129 | 0.01 < p < 0.05 |
| | 10 μM | 16614 | 699 | 3 | 123 | 0.01 < p < 0.05 |
| | 100 μM | 17861 | 945 | 3 | 132 | 0.01 < p < 0.05 |
| | 300 μM | 14498 | 1047 | 3 | 108 | p > 0.05 |
| Compound 21 | 1 μM | 18416 | 1507 | 3 | 142 | 0.01 < p < 0.05 |
| | 10 μM | 17611 | 717 | 3 | 136 | 0.01 < p < 0,05 |
| | 100 μM | 17796 | 1682 | 3 | 137 | p > 0.05 |
| | 300 μM | 17429 | 665 | 3 | 134 | 0.01 < p < 0.05 |

The values measured are given in counts per minute (cpm)

sd: standard deviation p: confidence interval n: replicates

The results show that:

the compounds 1 and 5 stimulate the incorporation of radioactive glucosamine at the concentration of 1 μM;

the compounds 2 and 13 stimulate the incorporation of radioactive glucosamine at the concentration of 10 μM;

the compound 9 stimulates the incorporation of radioactive glucosamine at the concentration of 300 μM;

the compound 17 stimulates the incorporation of radioactive glucosamine at the concentrations of 1, 10 and 100 μM;

the compound 21 stimulates the incorporation of radioactive glucosamine at the concentrations of 1, 10 and 300 μM.

Thus, the compounds (I) tested stimulate the incorporation of radioactive glucosamine, thereby indicating neosynthesis of glycosaminoglycans.

The invention claimed is:

1. A cosmetic composition comprising at least one compound of formula (I):

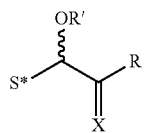

wherein
S* denotes a saccharide sugar radical from a saccharide chosen from glucose, galactose, mannose, xylose, lactose and rhamnose, said saccharide radical being connected to the rest of the molecule by a bond between the $C_1$ carbon atom of one of the sugars of said saccharide radical, this bond possibly being α or β anomeric;

X represents an oxygen;

R' represents i) a hydrogen atom; or ii) a $(C_1-C_6)$alkyl group;

R represents a group chosen from hydroxyl; saturated or unsaturated $(C_1-C_{18})$alkoxy, $NR_1R_2$ with $R_1$ and $R_2$, which may be identical or different, representing a hydrogen atom or an alkyl group.

2. The cosmetic composition as claimed in claim 1, wherein the at least one compound is chosen from the following compounds:

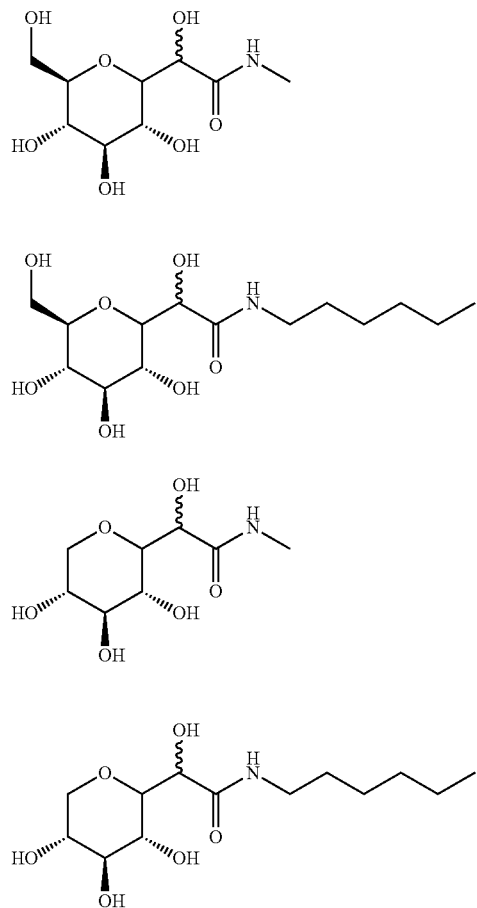

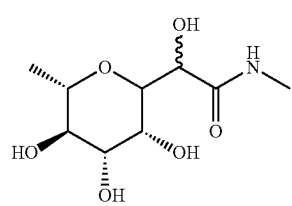

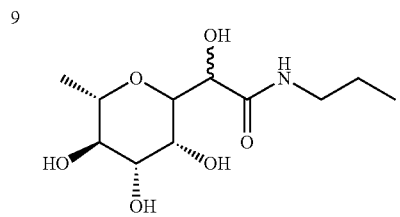

-continued
11
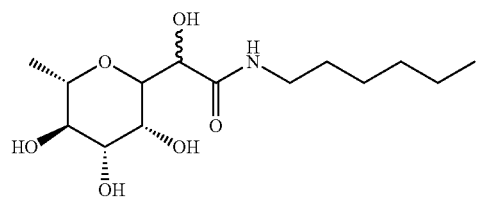
12
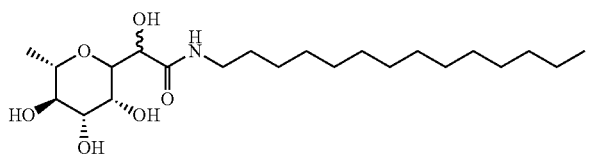
13
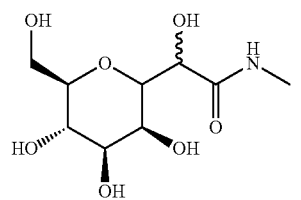
14
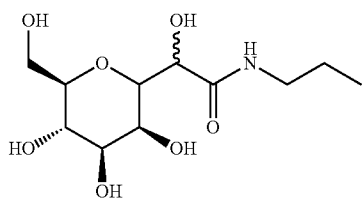
15
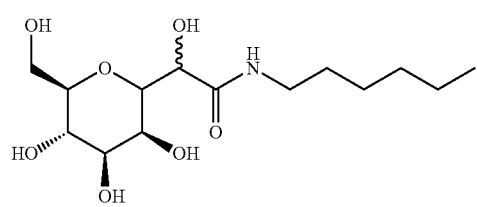
16
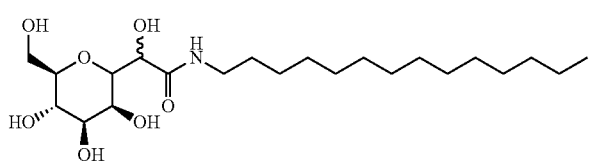
17
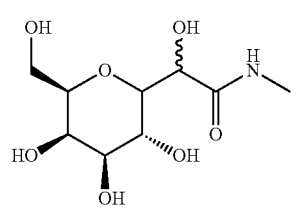
18
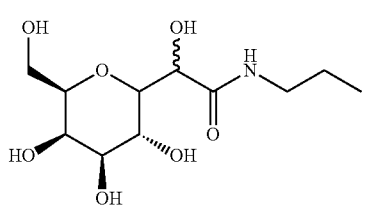
19
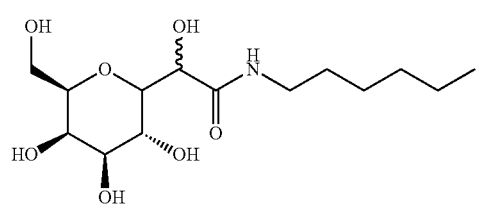
20
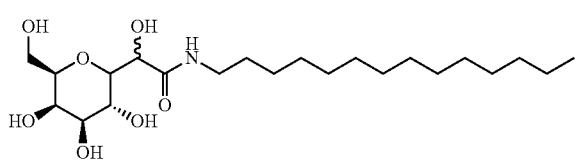 [SMILES: CCCCCCCCCCCCCCNC(=O)C(O)C1O[C@H](CO)[C@@H](O)[C@H](O)[C@H]1O]
21
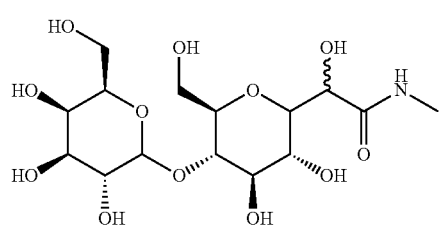
22
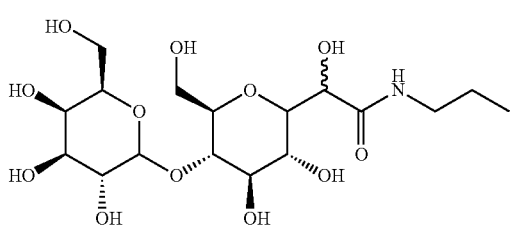
23
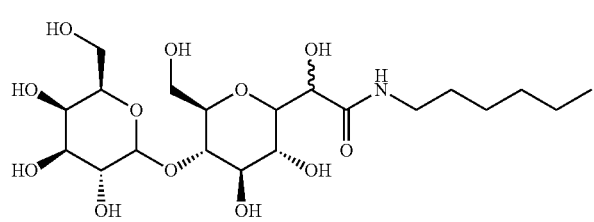

-continued
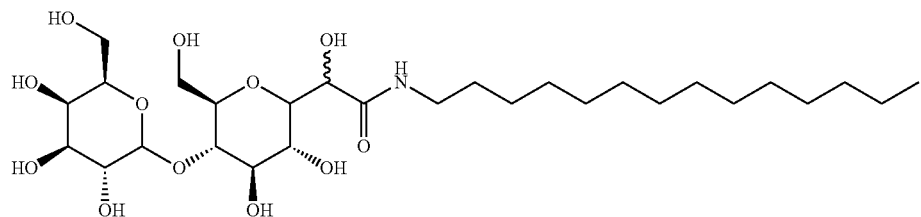
24
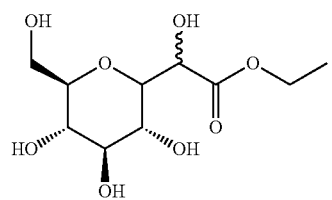
25
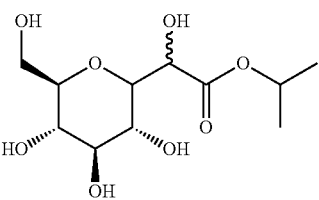
26
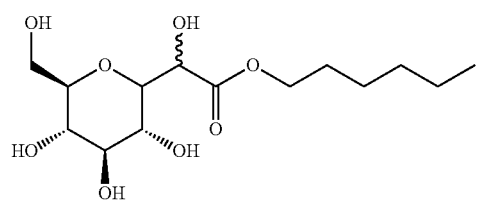
27
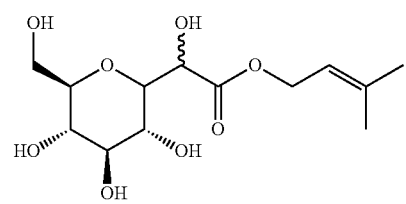
28
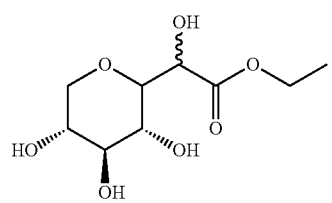
29
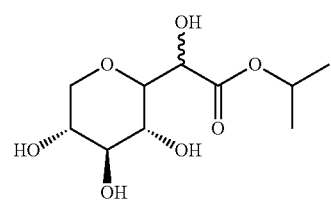
30
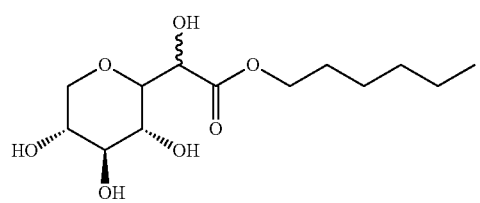
31
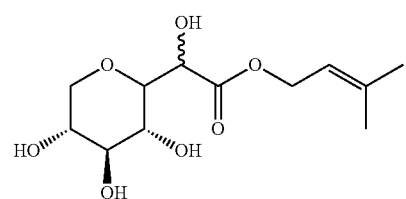
32
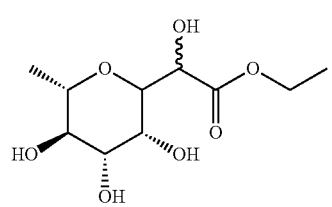
33
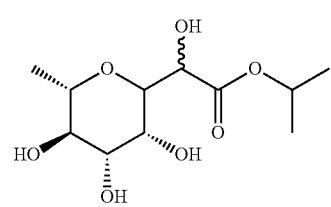
34
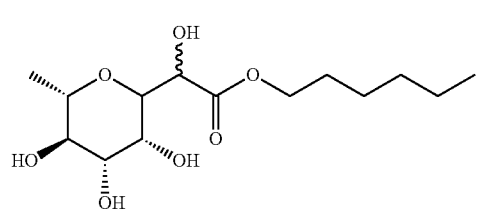
35
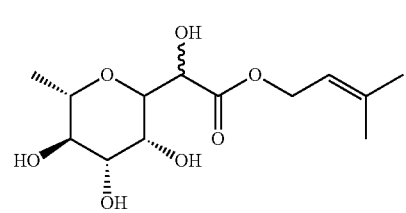
36

-continued
| | |
|---|---|
| 37 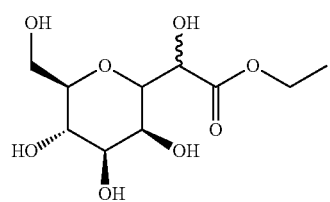 | 38 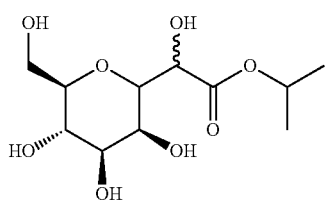 |
| 39 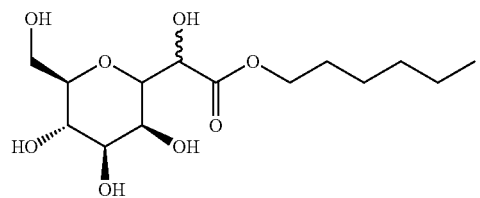 | 40 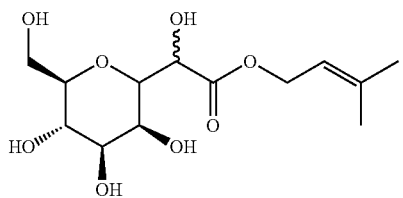 |
| 41 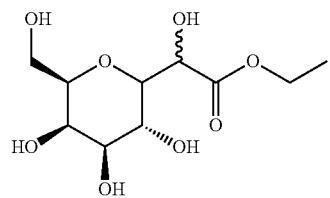 | 42 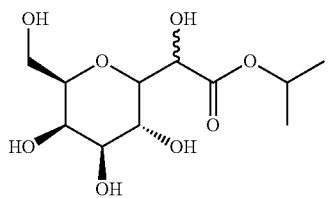 |
| 43 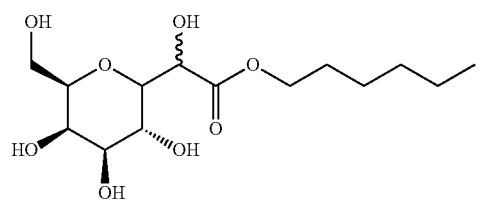 | 44 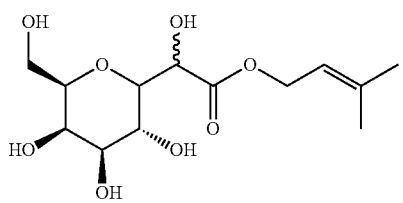 |
| 45 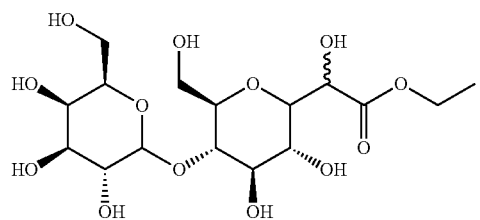 | 46 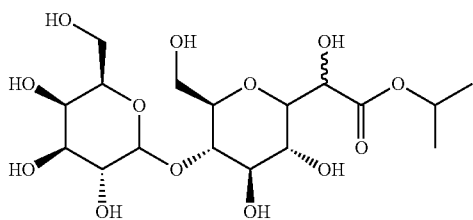 |
| 47 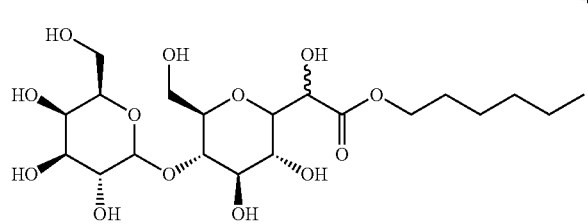 | 48 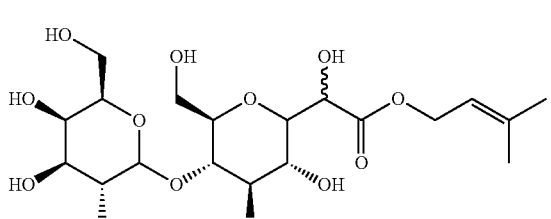 |
| 49 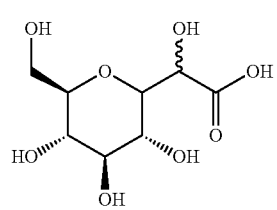 | 50 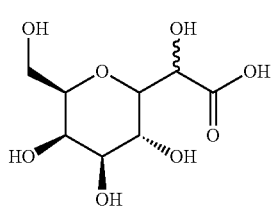 |

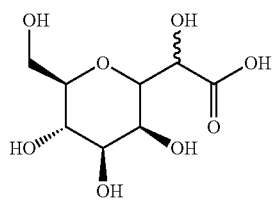
51
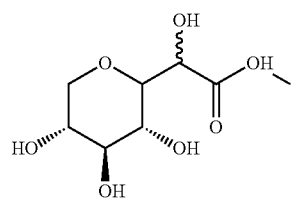

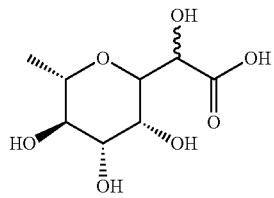
53
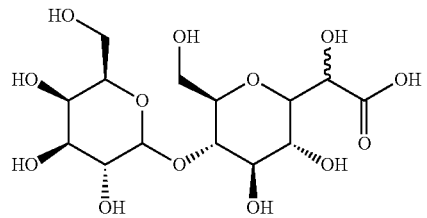

20 and also the solvates thereof, and the organic or mineral base or acid salts thereof, and also the substituted forms thereof in which all the hydroxyl groups of the sugar are substituted with the same group chosen from acetyl, tetrahydropyranyl (THP, trimethylsilyl (TMS, tert-butyldimethylsilyl (TBDMS), tosyl, tert-butyl, methoxymethyl (MOM) and benzoate.

3. The cosmetic composition as claimed in claim 1, wherein the at least one compound is chosen from:

1
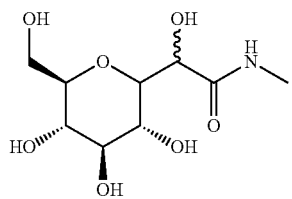
2
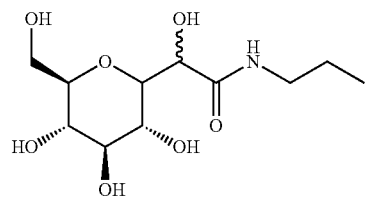

5
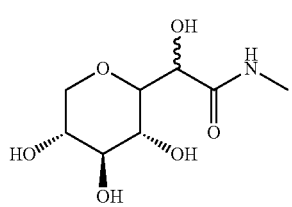
6
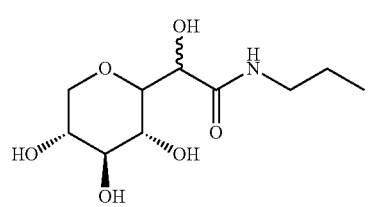

9
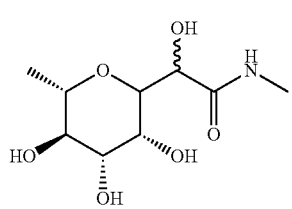
10
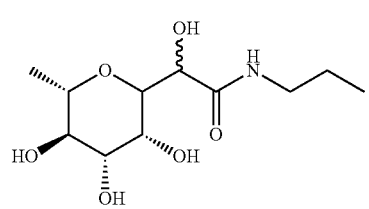

13
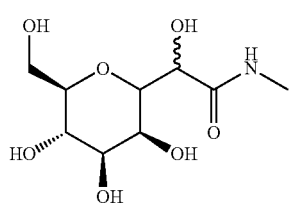
14
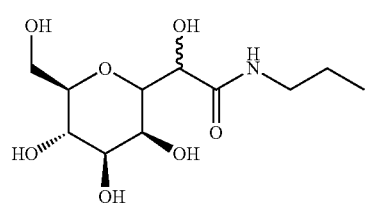

-continued

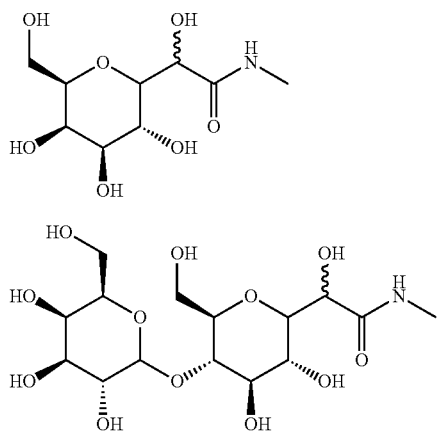

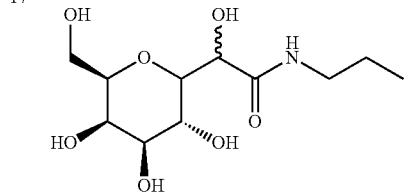

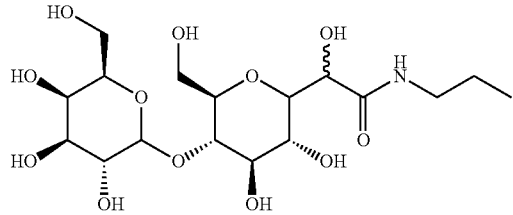

and also the solvates thereof, and the organic or mineral base or acid salts thereof.

4. The cosmetic composition as claimed in claim 1, which comprises a physiologically acceptable medium and at least one adjuvant in an amount of 0.1% to 40% by weight relative to the total weight of the composition.

5. The cosmetic composition as claimed in claim 4, wherein the physiologically acceptable medium and/or at least one adjuvant is selected from the group of water; organic solvents; carbon-based and/or silicone oils, of mineral, animal and/or plant origin; waxes, pigments, fillers, dyes, surfactants, emulsifiers, coemulsifiers; cosmetic or dermatological active agents, UV-screening agents, polymers, hydrophilic or lipophilic gelling agents, thickeners, preservatives, fragrances, bactericides, odour absorbers and antioxidants.

6. The cosmetic composition as claimed in claim 1, wherein the at least one compound is chosen from the following compounds:

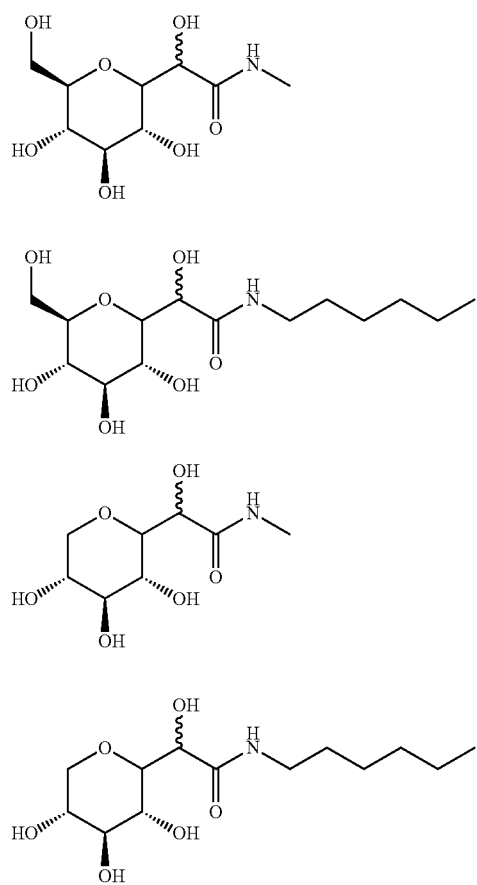

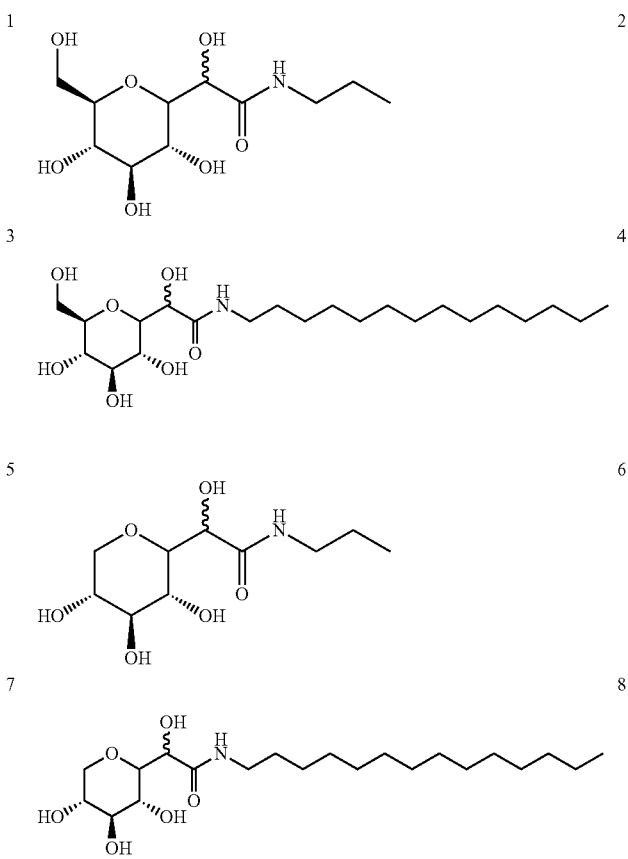

-continued
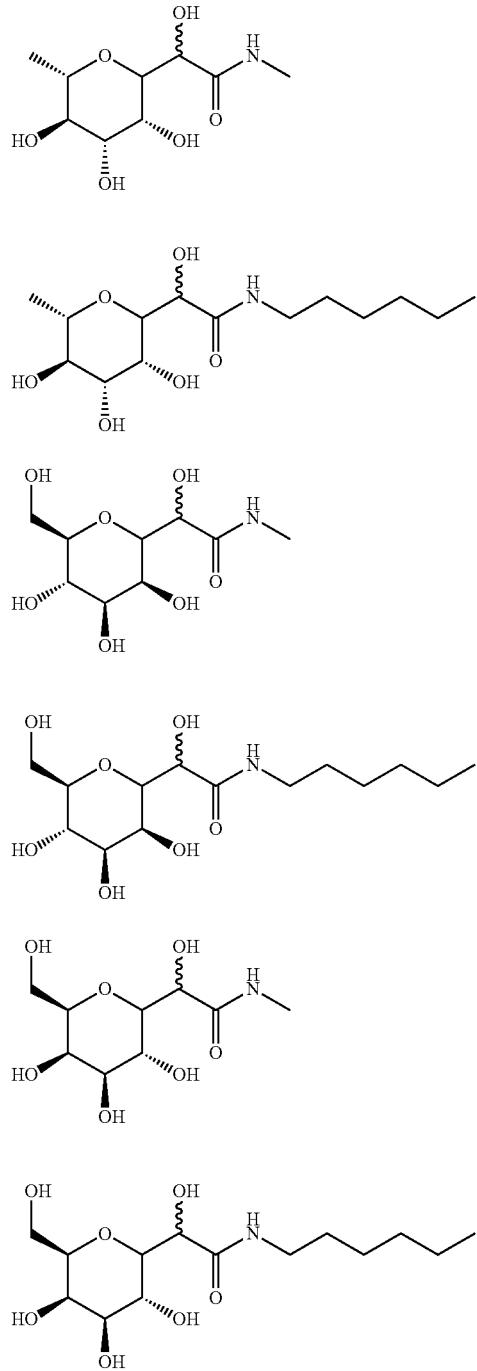
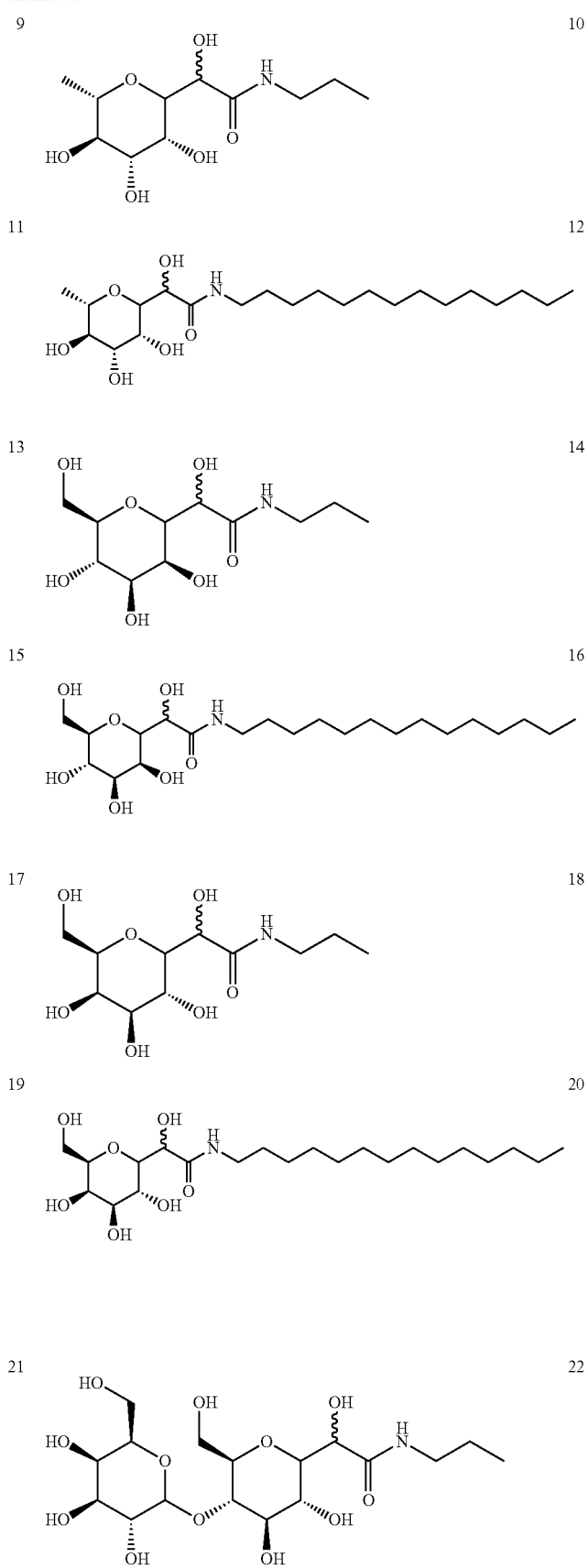

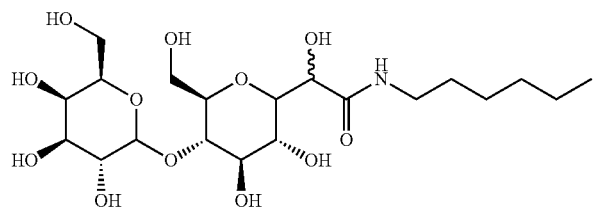
23
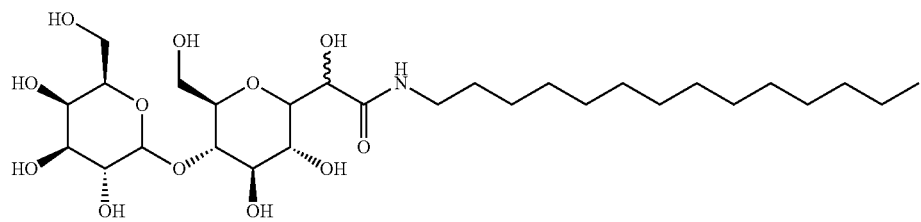
24
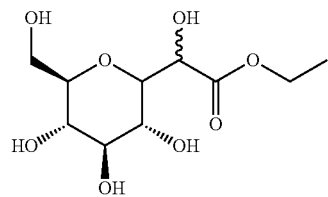
25
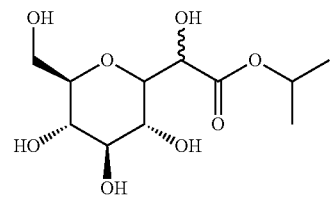
26
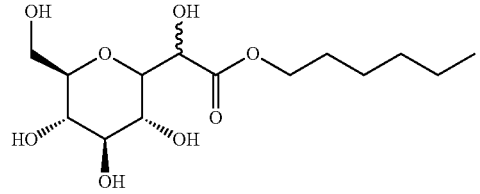
27
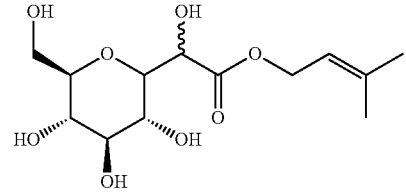
28
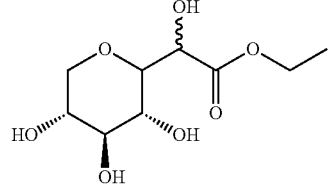
29
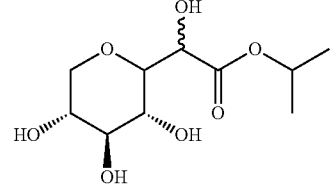
30
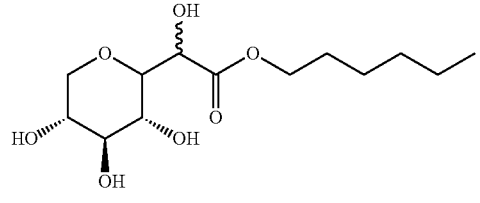
31
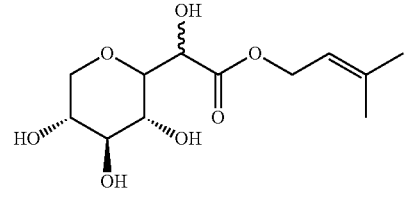
32
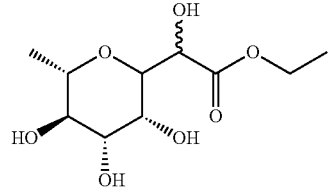
33
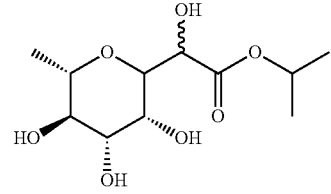
34

-continued
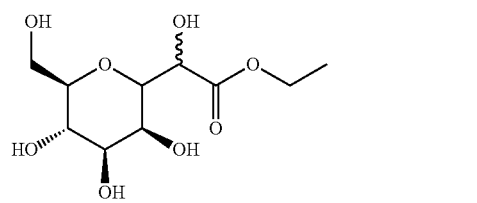
35
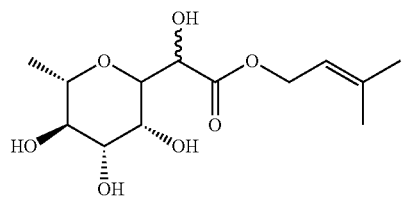
36
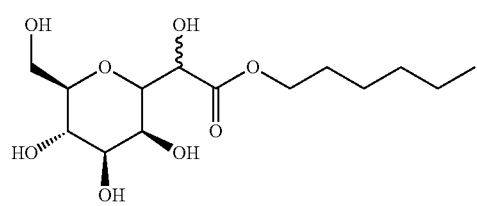
37
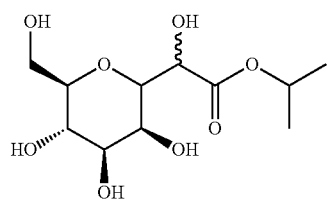
38
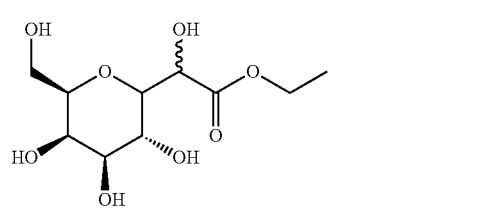
39
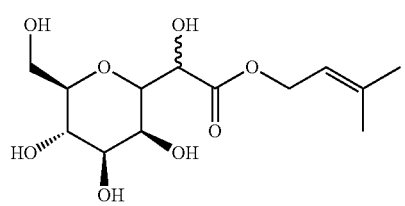
40
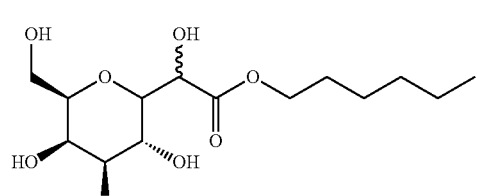
41
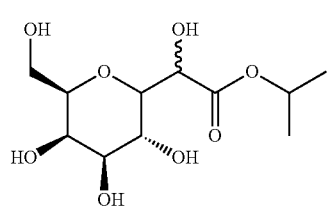
42
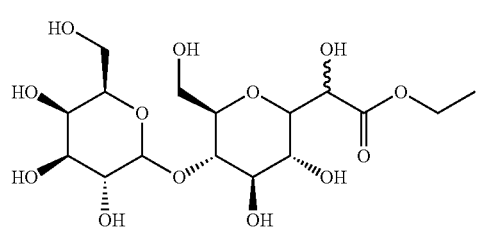
43
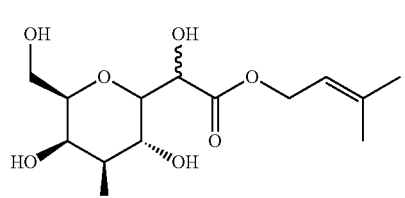
44
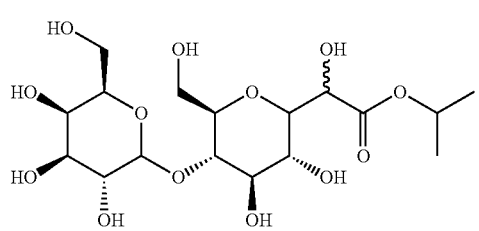
45
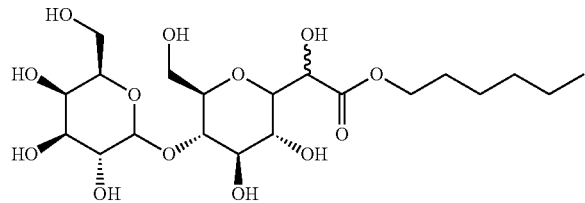
46
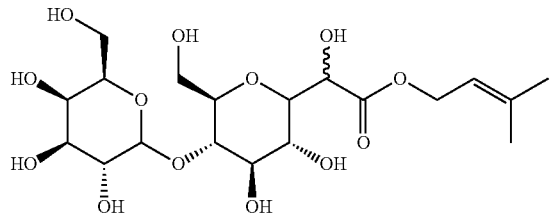
47
48

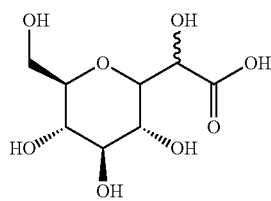
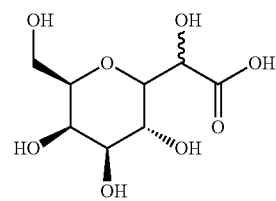
49
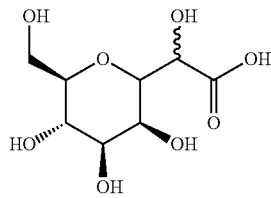
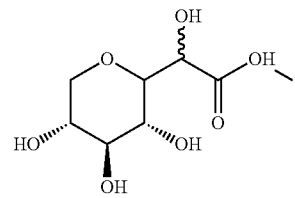
51
50
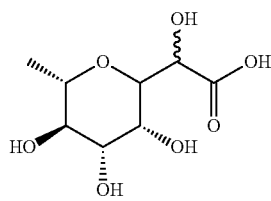
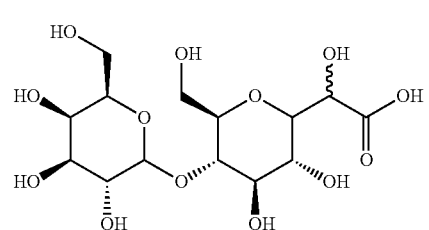
53
52
54
and also the solvates thereof, and the organic or mineral base or acid salts thereof.
7. The cosmetic composition as claimed in claim 2, wherein all of the hydroxyl groups of the sugar of the at least one compound are substituted with acetyl.
* * * * *